United States Patent
Esteller et al.

(10) Patent No.: US 12,179,024 B2
(45) Date of Patent: Dec. 31, 2024

(54) METHODS AND SYSTEMS FOR TARGET LOCALIZATION AND DBS THERAPY

(71) Applicant: Boston Scientific Neuromodulation Corporation, Valencia, CA (US)

(72) Inventors: Rosana Esteller, Santa Clarita, CA (US); Mahsa Malekmohammadi, Sherman Oaks, CA (US); Andrew Haddock, Los Angeles, CA (US); Tianhe Zhang, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/483,265

(22) Filed: Oct. 9, 2023

(65) Prior Publication Data

US 2024/0033526 A1 Feb. 1, 2024

Related U.S. Application Data

(63) Continuation of application No. 17/653,814, filed on Mar. 7, 2022, now Pat. No. 11,813,458.
(Continued)

(51) Int. Cl.
*A61N 1/05* (2006.01)
*A61N 1/36* (2006.01)

(52) U.S. Cl.
CPC ......... *A61N 1/3614* (2017.08); *A61N 1/0534* (2013.01)

(58) Field of Classification Search
CPC ...... A61N 1/3614; A61N 1/0534; A61N 1/08; A61N 1/36067; A61N 1/36185;
(Continued)

(56) References Cited

U.S. PATENT DOCUMENTS 6,052,624 A 4/2000 Mann
6,181,969 B1 1/2001 Gord
(Continued)

FOREIGN PATENT DOCUMENTS

AU 2014351064 7/2019
AU 2019216650 9/2019
(Continued)

OTHER PUBLICATIONS

Frankemolle, Anneke M.M., "Reversing Cognitive-Motor Impairments in Parkinson's Disease Patients Using a Computational Modelling Approach to Deep Brain Stimulation Programming," Brain—A Journal of Neurology, 133, 2010, pp. 746-761.
(Continued)

*Primary Examiner* — Ankit D Tejani
*Assistant Examiner* — Joshua Brendon Solomon
(74) *Attorney, Agent, or Firm* — Lewis & Reese, PLLC

(57) ABSTRACT

Methods and systems are described for detecting if a stimulation lead implanted in a patient's brain has moved. Lead movement occurring between a first time and a second time may be determined by comparing features extracted from evoked potentials recorded at the two times. The disclosed methods and systems are particularly useful for determining if a stimulation lead has moved between the time it was implanted in the patient's brain and the time that stimulation parameters are being optimized. Lead movement during implantation, during parameter optimization, and during or between other lead optimization processes may be determined as well.

20 Claims, 19 Drawing Sheets

Related U.S. Application Data

(60) Provisional application No. 63/263,634, filed on Nov. 5, 2021, provisional application No. 63/162,887, filed on Mar. 18, 2021.

(58) Field of Classification Search
CPC .. A61N 2001/083; A61B 5/065; A61B 5/686; A61B 5/377
See application file for complete search history.

(56) References Cited

U.S. PATENT DOCUMENTS

| | | | |
|---|---|---|---|
| 6,393,325 B1 | 5/2002 | Mann et al. |
| 6,490,486 B1 | 12/2002 | Bradley |
| 6,609,032 B1 | 8/2003 | Woods et al. |
| 6,845,267 B2 | 1/2005 | Harrison et al. |
| 6,909,917 B2 | 6/2005 | Woods et al. |
| 6,950,707 B2 | 9/2005 | Whitehurst |
| 7,555,346 B1 | 6/2009 | Woods et al. |
| 7,582,062 B2 | 9/2009 | Magill et al. |
| 7,831,307 B1 | 11/2010 | Moffitt |
| 7,930,030 B2 | 4/2011 | Woods et al. |
| 8,121,701 B2 | 2/2012 | Woods et al. |
| 8,180,601 B2 | 5/2012 | Butson et al. |
| 8,265,762 B2 | 9/2012 | Woods et al. |
| 8,401,658 B2 | 3/2013 | Woods et al. |
| 8,606,362 B2 | 12/2013 | He et al. |
| 8,620,436 B2 | 12/2013 | Parramon et al. |
| 8,805,524 B2 | 8/2014 | Woods et al. |
| 8,812,124 B2 | 8/2014 | Lee |
| 8,855,773 B2 | 10/2014 | Kokones et al. |
| 8,868,193 B2 | 10/2014 | Ranu et al. |
| 8,868,196 B2 | 10/2014 | Lee et al. |
| 8,868,197 B2 | 10/2014 | Lee |
| 8,909,350 B2 | 12/2014 | Lee |
| 8,914,119 B2 | 12/2014 | Wu et al. |
| 8,958,615 B2 | 2/2015 | Blum et al. |
| 9,014,820 B2 | 4/2015 | Lee et al. |
| 9,050,473 B2 | 6/2015 | Woods et al. |
| 9,072,905 B2 | 7/2015 | Kokones et al. |
| 9,205,261 B2 | 12/2015 | Kim et al. |
| 9,248,280 B2 | 2/2016 | Moffitt et al. |
| 9,381,356 B2 | 7/2016 | Parker et al. |
| 9,387,328 B2 | 7/2016 | Lee |
| 9,387,334 B2 | 7/2016 | Lee et al. |
| 9,411,935 B2 | 8/2016 | Moffitt et al. |
| 9,511,231 B1 | 12/2016 | Kent et al. |
| 10,183,167 B2 | 1/2019 | Steinke et al. |
| 10,183,168 B2 | 1/2019 | Baru et al. |
| 10,195,439 B2 | 2/2019 | Steinke et al. |
| 10,207,113 B2 | 2/2019 | Lee et al. |
| 10,207,114 B2 | 2/2019 | Lee |
| 10,249,041 B2 | 4/2019 | Varkuti |
| 10,252,059 B2 | 4/2019 | Steinke et al. |
| 10,286,205 B2 | 5/2019 | Steinke et al. |
| 10,406,368 B2 | 9/2019 | Hershey et al. |
| 10,463,860 B2 | 11/2019 | Sinclair et al. |
| 10,549,097 B2 | 2/2020 | Zhang et al. |
| 10,576,292 B2 | 3/2020 | Orinski |
| 10,974,051 B2 | 4/2021 | Steinke et al. |
| 10,994,131 B2 | 5/2021 | Durand et al. |
| 11,020,004 B2 | 6/2021 | Varkuti |
| 11,123,563 B2 | 9/2021 | Mustakos et al. |
| 11,195,609 B2 | 12/2021 | Mustakos et al. |
| 11,344,732 B2 | 5/2022 | Moffitt et al. |
| 11,376,433 B2 | 7/2022 | Zhang et al. |
| 11,478,633 B2 | 10/2022 | Tinkhauser et al. |
| 2005/0065427 A1 | 3/2005 | Magill et al. |
| 2006/0224222 A1 | 10/2006 | Bradley et al. |
| 2007/0244407 A1 | 10/2007 | Osorio |
| 2009/0118786 A1 | 5/2009 | Meadows et al. |
| 2009/0118787 A1 | 5/2009 | Moffitt et al. |
| 2009/0299421 A1 | 12/2009 | Sawchuk |
| 2010/0305660 A1 | 12/2010 | Hegi et al. |
| 2011/0105939 A1 | 5/2011 | Yong et al. |
| 2012/0046712 A1 | 2/2012 | Woods et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0163639 A1 | 6/2014 | Zhu |
| 2014/0243926 A1 | 8/2014 | Carcieri |
| 2014/0277282 A1 | 9/2014 | Jaax |
| 2014/0378941 A1 | 12/2014 | Su et al. |
| 2015/0039048 A1 | 2/2015 | Woods et al. |
| 2015/0066108 A1* | 3/2015 | Shi ............ A61N 1/0534 607/59 |
| 2015/0080982 A1 | 3/2015 | Funderburk |
| 2015/0088228 A1 | 3/2015 | Moffitt |
| 2015/0157861 A1 | 6/2015 | Aghassian |
| 2015/0231402 A1 | 8/2015 | Aghassian |
| 2015/0360033 A1 | 12/2015 | Koubeissi et al. |
| 2015/0360038 A1 | 12/2015 | Zottola et al. |
| 2016/0045747 A1 | 2/2016 | Jiang et al. |
| 2016/0158565 A1* | 6/2016 | Lee ............ A61N 1/3616 607/59 |
| 2016/0287126 A1 | 10/2016 | Parker et al. |
| 2016/0339251 A1 | 11/2016 | Kent et al. |
| 2016/0361542 A1 | 12/2016 | Kaula et al. |
| 2017/0120056 A1 | 5/2017 | Woods et al. |
| 2017/0189687 A1 | 7/2017 | Steinke et al. |
| 2017/0189689 A1 | 7/2017 | Steinke et al. |
| 2017/0281959 A1 | 10/2017 | Serrano Carmona et al. |
| 2017/0333701 A1 | 11/2017 | Bradley et al. |
| 2017/0333715 A1 | 11/2017 | De Ridder et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0110987 A1 | 4/2018 | Parker |
| 2018/0132747 A1 | 5/2018 | Parker et al. |
| 2018/0133459 A1 | 5/2018 | Parker et al. |
| 2018/0140831 A1 | 5/2018 | Feldman et al. |
| 2018/0140843 A1 | 5/2018 | Kent et al. |
| 2018/0221644 A1 | 8/2018 | Grill et al. |
| 2019/0030323 A1 | 1/2019 | Koka et al. |
| 2019/0038902 A1 | 2/2019 | Kaemmerer et al. |
| 2019/0070418 A1 | 3/2019 | Hincapie Ordonez et al. |
| 2019/0076645 A1 | 3/2019 | Bower et al. |
| 2019/0083796 A1 | 3/2019 | Weerakoon et al. |
| 2019/0099602 A1 | 4/2019 | Esteller et al. |
| 2019/0143120 A1 | 5/2019 | Sinclair et al. |
| 2019/0175915 A1 | 6/2019 | Brill et al. |
| 2019/0209844 A1 | 7/2019 | Esteller et al. |
| 2019/0209851 A1 | 7/2019 | Kothandaraman et al. |
| 2019/0232062 A1 | 8/2019 | Falowski |
| 2019/0262609 A1 | 8/2019 | Brill et al. |
| 2019/0274637 A1 | 9/2019 | Wilson et al. |
| 2019/0275331 A1 | 9/2019 | Zhu |
| 2019/0299006 A1 | 10/2019 | Marnfeldt |
| 2019/0366094 A1 | 12/2019 | Esteller et al. |
| 2019/0381318 A1 | 12/2019 | Sinclair et al. |
| 2020/0001086 A1 | 1/2020 | Fernandez et al. |
| 2020/0001091 A1 | 1/2020 | Marnfeldt |
| 2020/0038660 A1 | 2/2020 | Torgerson |
| 2020/0138324 A1 | 5/2020 | Sinclair et al. |
| 2020/0147393 A1 | 5/2020 | Zhang et al. |
| 2020/0305744 A1 | 10/2020 | Weerakoon et al. |
| 2020/0305745 A1 | 10/2020 | Wagenbach et al. |
| 2020/0335221 A1 | 10/2020 | Fichtinger et al. |
| 2020/0391037 A1 | 12/2020 | Grado et al. |
| 2021/0016091 A1 | 1/2021 | Parker et al. |
| 2021/0046322 A1 | 2/2021 | Zhang et al. |
| 2021/0121696 A1 | 4/2021 | Parker et al. |
| 2021/0236821 A1 | 8/2021 | Sinclair et al. |
| 2021/0267523 A1 | 9/2021 | Donoghue et al. |
| 2021/0339014 A1 | 11/2021 | Dinsmoor et al. |
| 2022/0040486 A1 | 2/2022 | Moffitt |
| 2022/0111213 A1 | 4/2022 | Cassar et al. |
| 2022/0151535 A1 | 5/2022 | Parker et al. |
| 2022/0218995 A1 | 7/2022 | Block et al. |
| 2022/0233866 A1 | 7/2022 | Gururaj et al. |
| 2022/0266022 A1 | 8/2022 | Steinke et al. |
| 2022/0296892 A1 | 9/2022 | Esteller et al. |
| 2022/0296893 A1 | 9/2022 | Steinke et al. |

(56) References Cited

U.S. PATENT DOCUMENTS

| | | |
|---|---|---|
| 2022/0339448 A1 | 10/2022 | Jayakumar et al. |
| 2023/0023842 A1 | 1/2023 | Steinke et al. |
| 2023/0062062 A1 | 3/2023 | Litvak et al. |
| 2023/0069981 A1 | 3/2023 | Isaacson et al. |
| 2023/0099390 A1 | 3/2023 | Esteller et al. |
| 2023/0141183 A1 | 5/2023 | Moore et al. |
| 2023/0201597 A1 | 6/2023 | Haddock et al. |
| 2023/0271015 A1 | 8/2023 | Malekmohammadi et al. |

FOREIGN PATENT DOCUMENTS

| | | |
|---|---|---|
| CN | 107280665 A | 10/2017 |
| EP | 3229891 | 8/2019 |
| WO | 2016/205231 | 12/2016 |
| WO | 2018/008034 | 1/2018 |
| WO | 2018/163178 | 9/2018 |
| WO | 2018/213872 | 11/2018 |
| WO | 2019/070406 | 4/2019 |
| WO | 2019/210371 | 11/2019 |
| WO | 2019/211314 | 11/2019 |
| WO | 2019/217079 | 11/2019 |
| WO | 2020/223165 | 11/2020 |
| WO | 2021/026151 | 2/2021 |
| WO | 2021/080727 | 4/2021 |

OTHER PUBLICATIONS

Gmel, Gerrit E., et al., "A New Biomarker for Closed-Loop Deep Brain Stimulation in the Subthalamic Nucleus for Patients with Parkinson's Disease," IEEE Biomedical Circuits and Systems Conference (BioCAS) Proceedings, Lausanne, 2014, pp. 500-503.

Gmel, Gerrit E., et al., "A New Biomarker for Subthalamic Deep Brain Stimulation for Patients with Advanced Parkinson's Disease—A Pilot Study," J. Neural Eng., 12, 2015, 11 pages.

Gmel, Gerrit Eduard, "Evoked Brain Neural Potentials," Dissertation for The University of New South Wales, Sep. 2016, 231 pages.

Kent, Alexander Rafael, et al., "Characterization of Evoked Potentials During Deep Brain Stimulation in the Thalamus," Dissertation Submitted in the Department of Biomedical Engineering Duke University, 2013, 320 pages.

Kent, Alexander R., et al., "Neural Origin of Evoked Potentials During Thalamic Deep Brain Stimulation," J Neurophysiol, 110, 2013, pp. 826-843.

Kent, A.R., et al., "Recording Evoked Potentials During Deep Brain Stimulaton: Development and Validation of Instrumentation to Suppress to Stimulus Artefact," J Neural Eng., 9(3), Jun. 2012, 30 pages.

Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.

Laarne, Paivi, et al., "Accuracy of Two Dipolar Inverse Algorithms Applying Reciprocity for Forward Calculation," Computers and Biomedical Research, vol. 33, Issue 3, pp. 172-185, Jun. 2000.

Moffitt, Michael A., et al., "Electrical Localization of Neural Activity in the Dorsal Horn of the Spinal Cord: A Modeling Study," Annals of Biomedical Engineering, 32(12), pp. 1694-1709, 2004.

Pascual-Marqui, RD, "Standardized Low-Resolution Brain Electromagnetic Tomography (sLORETA): Technical Details," Methods Find Exp Clin Pharmacol, 24 Suppl D, 5-12. 2002.

Sinclair, Nicholas C., et al., "Subthalamic Nucleus Deep Brain Stimulation Evokes Resonant Neural Activity," Annals of Neurology, 83(5), pp. 1027-1031, May 4, 2018.

Sinclair, Nicholas C., et al., "Subthalamic Nucleus Deep Brain Stimulation Evokes Resonant Neural Activity," Poster, 2019, 1 page.

Sinclair, Nicholas C., et al., "Deep Brain Stimulation for Parkinson's Disease Modulates High-Frequency Evoked and Spontaneous Neural Activity," Neurobiology of Disease, vol. 130, 104522, Oct. 2019.

Sinclair, Nicholas C., et al., "On the Neural Basis of Deep Brain Stimulation Evoked Resonant Activity," Biomed. Phys. Eng. Express, 5, 2019, 9 pages.

Sinclair, Nicholas C., et al., "Directional Deep Brain Stimulation Evoked Resonant Neural Activity (ERNA)," Poster, 2020, 1 page.

Thevathasan, Wesley, et al., "Tailoring Subthalamic Nucleus Deep Brain Stimulation for Parkinson's Disease Using Evoked Resonant Neural Activity," Frontiers in Human Neuroscience, vol. 14, Article 71, Feb. 2020, 6 pages.

Walker, Harrison, MD, et al., Directional Subthalamic Nucleus DBS for Parkinson's Disease: Year 3 Interim Analyses, UAB Medicine Poster, 2020, 1 page.

Wiest, C. et al., "Local Field Potential Activity Dynamics in Response to Deep Brain Stimulation of the Subthalamic Nucleus in Parkinson's Disease," Neurobiology of Disease, 143, 2020, 15 pages.

Wiest, C., et al., "Subthalamic Deep Brain Stimulation Induces Finely-Tuned Gamma Oscillations in the Absence of Levodopa," Neurobiology of Disease, 152, 105287, 2021, 13 pages.

Georgopoulos, Apostolos P., et al., "On the Relations Between the Direction of Two-Dimensional Arm Movements and Cell Discharge in Primate Motor Cortex," The Journal of Neuroscience, vol. 2, No. 11, pp. 1527-1537, 1982.

Hatsopoulos, Nicholas G. et al., "Sensing with the Motor Cortex," J. Neuron, 72(3), 22 pages, 2011.

Shils, Jay, et al., "Motor Evoked Potential Recordings During Segmented DBS—A Feasibility Study," Oper Neurosurg (Hagerstown), Mar. 1, 20215, 20(4), pp. 419-425.

Wiest, C., et al., "Local Field Potential Activity Dynamics in Response to Deep Brain Stimulation of the Subthalamic Nucleus in Parkinson's Disease." Neurobiology of Disease, 2019, 41 pages.

Zelmann, Rina, et al., "Automatic Optimization of Depth Electrode Trajectory Planning," Montreal Neurological Institute Neurology and Neurosurgery, CLIP 2013, LNCS 8361, 2014, pp. 99-104.

Beriault, Silvain, et al., "A Multi-Modal Approach to Computer-Assisted Deep Brain Stimulation Trajectory Planning," International Journal of Computer Assisted Radiology and Surgery, 7, 2012, pp. 687-704.

Beriault, Silvain, et al., "A Prospective Evaluation of Computer-Assisted Deep Brain Stimulation Trajectory Planning," Montreal Neurological Institute McConnell Brain Imaging Centre, CLIP 2012, LNCS 7761, 2013, pp. 42-49.

Qian, Xing, et al., "A Method for Removal of Deep Brain Stimulation Artifact From Local Field Potentials," IEEE Transactions On Neural Systems and Rehabilitation Engineering, vol. 25, No. 12, Dec. 2017, 10 pages.

\* cited by examiner

METHODS AND SYSTEMS FOR TARGET LOCALIZATION AND DBS THERAPY

CROSS REFERENCE TO RELATED APPLICATIONS

This application is a continuation of U.S. Non-Provisional application Ser. No. 17/653,814, filed Mar. 7, 2022 (now allowed), which is a non-provisional application of U.S. Provisional Patent Application Ser. No. 63/263,634, filed Nov. 5, 2021, and U.S. Provisional Patent Application Ser. No. 63/162,887, filed Mar. 18, 2021. All of these applications are incorporated herein by reference, and priority is claimed to them.

FIELD OF THE INVENTION

This application relates to deep brain stimulation (DBS), and more particularly, to methods and systems for using sensed neural responses for facilitating aspects of DBS.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS). DBS has been applied therapeutically for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707. However, the present invention may find applicability with any implantable neurostimulator device system.

Each of these neurostimulation systems, whether implantable or external, typically includes one or more electrode carrying stimulation leads, which are implanted at the desired stimulation site, and a neurostimulator, used externally or implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects. For example, bilateral DBS of the subthalamic nucleus has been shown to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., Reversing Cognitive-Motor Impairments in Parkinson's Disease Patients Using a Computational Modelling Approach to Deep Brain Stimulation Programming, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC) or mobile platform. The PC or custom hardware may actively control the characteristics of the electrical stimulation generated by the neurostimulator to allow the optimum stimulation parameters to be determined based on patient feedback, including both, but not limited to, behavioral and clinical response, anatomical and neurophysiological information and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. The system may also instruct the user how to improve the positioning of the leads, or confirm when a lead is well-positioned. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

In the context of DBS, the brain is dynamic (e.g., due to disease progression, motor re-learning, pneumocephalus (brain shift) during implantation surgical procedure, the development of scar tissue in the region of the implanted leads, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. In particular, a patient's stimulation needs may be impacted by their medication state. Additionally, the need for stimulation and/or medication may fluctuate across the day and week, depending on activities of daily living, especially sleep and activity. Moreover, brain diseases treated by DBS, such as Parkinson's disease, may be multi-faceted with respect to their symptomatic profiles (for example rigidity vs tremor in Parkinson disease), and optimal treatments may be different when addressing one symptom to another.

Thus, there is a need for methods and systems that assist a clinician in obtaining an optimum lead placement during implantation process and to determine optimum stimulation parameters for treating the patient. There is also a need for closed loop feedback that can be used to adjust stimulation parameters as the patient's stimulation needs change with time or based on their medication state.

SUMMARY

Disclosed herein is a method of assessing a decline in therapeutic efficacy of deep brain stimulation (DB S) in a patient having an electrode lead implanted in their brain, the electrode lead comprising a plurality of electrodes, the method comprising: providing stimulation to the patient using a first one or more of the plurality of electrodes, determining impedances at one or more of the plurality of electrodes, sensing evoked potentials evoked by the stimulation using one or more of the plurality of electrodes, and determining a cause of the decline in therapeutic efficacy based on both the impedances and the evoked potentials. According to some embodiments, determining a cause of the decline in therapeutic efficacy comprises comparing the impedances to baseline impedances. According to some embodiments, the baseline impedances are determined during implantation of the electrode lead into the patient's brain. According to some embodiments, the baseline impedances are determined during a fitting procedure. According to some embodiments, determining a cause of the decline in therapeutic efficacy comprises comparing the sensed evoked potentials to a baseline evoked potential. According to some embodiments, comparing the sensed evoked potentials to a baseline evoked potential comprises determining one or more features of the sensed evoked potentials and comparing the determined features to corresponding features of the baseline evoked potentials. According to some embodiments, the baseline evoked potentials are determined during implantation of the electrode lead into the patient's brain. According to some embodiments, the baseline evoked potentials are determined during a fitting procedure. According to some embodiments, determining the cause of the decline in therapeutic efficacy comprises determining if the cause is one or more of (a) migration of the electrode lead, (b) formation of scar tissue at one or more of the electrodes, and (c) progression of the patient's disease. According to some embodiments, the method further comprises communicating an indication of the cause of the decline in therapeutic efficacy. According to some embodiments, the communicating comprises communicating the indication of cause of the decline in therapeutic efficacy to an external device of the patient. According to some embodiments, the communicating comprises communicating the indication of the cause of the decline in therapeutic efficacy to a remote location via an internet connection. According to some embodiments, the method further comprises receiving an indication of the decline in therapy. According to some embodiments, the indication of the decline in therapy is provided by the patient via an external device. According to some embodiments, the indication of the decline in therapy is determined based on the evoked potential. According to some embodiments, the method further comprises determining a second one or more of the plurality of electrodes to provide stimulation. According to some embodiments, determining a second one or more of the plurality of electrodes to provide stimulation comprises: iteratively using one or more of the electrodes to provide stimulation at a plurality of stimulation locations upon the lead, sensing evoked potentials evoked by the stimulation at each of the stimulation locations, comparing the sensed evoked potentials for each of the stimulation locations to the baseline evoked potential, and selecting the stimulation location for which the sensed evoked potentials most closely match the baseline evoked potential. According to some embodiments, the method further comprises adjusting a stimulation location on the lead by: (a) determining an optimized stimulation waveform for evoking a detectable evoked potential by: using one or more of the electrodes to provide an initial stimulation waveform, determining if an evoked potential is detectable using one or more of the electrodes, if an evoked potential is not detectable, adjusting a parameter of the initial stimulation waveform until a first evoked potential is detectable, (b) determining an optimized longitudinal stimulation position along an axis of the lead by: providing stimulation at different longitudinal positions along the axis of the lead using the optimized stimulation waveform, recording a second evoked potential evoked by the stimulation at each of the longitudinal positions, and selecting the optimized longitudinal stimulation position based on the second evoked potential, and (c) determining an optimized rotational stimulation position about the axis of the lead by: at the selected optimized longitudinal stimulation position providing stimulation at different rotational positions about the axis of the lead using the optimized stimulation waveform, recording a third evoked potential evoked by the stimulation at each of the rotational positions, and selecting the optimized rotational stimulation position based on the third evoked potential.

Also disclosed herein is a medical device configured to assess a decline in therapeutic efficacy of deep brain stimulation (DBS) in a patient having an electrode lead implanted in their brain, the electrode lead comprising a plurality of electrodes, the device comprising: control circuitry configured to: cause stimulation circuitry to provide stimulation to the patient using one or more of the plurality of electrodes, determine impedances at one or more of the plurality of electrodes, sense evoked potentials evoked by the stimulation using one or more of the plurality of electrodes, and determine a cause of the decline in therapeutic efficacy based on both the impedances and the evoked potentials. According to some embodiments, determining a cause of the decline in therapeutic efficacy comprises comparing the impedances to baseline impedances. According to some embodiments, the baseline impedances are determined during implantation of the electrode lead into the patient's brain. According to some embodiments, the baseline impedances are determined during a fitting procedure. According to some embodiments, determining a cause of the decline in therapeutic efficacy comprises comparing the sensed evoked potentials to a baseline evoked potential. According to some embodiments, comparing the sensed evoked potentials to a baseline evoked potential comprises determining one or more features of the sensed evoked potentials and comparing the determined features to corresponding features of the baseline evoked potentials. According to some embodiments, the baseline evoked potentials are determined during implantation of the electrode lead into the patient's brain. According to some embodiments, the baseline evoked potentials are determined during a fitting procedure. According to some embodiments, the baseline evoked potentials are determined during a fitting procedure. According to some embodiments, determining the cause of the decline in therapeutic efficacy comprises determining if the cause is one or more of (a) migration of the electrode lead, (b) formation of scar tissue at one or more of the electrodes, and (c) progression of the patient's disease. According to some embodiments, the device is further configured to communicate an indication of the cause of the decline in therapeutic efficacy. According to some embodiments, the communicating comprises communicating the indication of the cause of the decline in therapeutic efficacy to an external device of the patient. According to some embodiments, the communicating comprises communicating the indication of the cause of the decline in therapeutic efficacy to a remote location via an internet connection. According to some embodiments, the device is further configured to receive an indication of the decline in therapy. According to some embodiments, the indication of the decline in therapy is provided by the patient via an external device. According to some embodiments, the indication of the decline in therapy is determined based on the evoked potential. According to some embodiments, the control circuitry is further configured to determine a second one or more of the plurality of electrodes to provide stimulation. According to some embodiments, determining a second one or more of the plurality of electrodes to provide stimulation comprises: iteratively using one or more of the electrodes to provide stimulation at a plurality of stimulation locations upon the lead, sensing evoked potentials evoked by the stimulation at each of the stimulation locations, comparing the sensed evoked potentials for each of the stimulation locations to the baseline evoked potential, and selecting the stimulation location for which the sensed evoked potentials most closely match the baseline evoked potential. According to some embodiments, the control circuitry is further configured to adjust a stimulation location on the lead by: (a) determining an optimized stimulation waveform for evoking a detectable evoked potential by: using one or more of the electrodes to provide an initial stimulation waveform, determining if an evoked potential is detectable using one or more of the electrodes, if an evoked potential is not detectable, adjusting a parameter of the initial stimulation waveform until a first evoked potential is detectable, (b) determining an optimized longitudinal stimulation position along an axis of the lead by: providing stimulation at different longitudinal positions along the axis of the lead using the optimized stimulation waveform, recording a second evoked potential evoked by the stimulation at each of the longitudinal positions, and selecting the optimized longitudinal stimulation position based on the second evoked potential, and (c) determining an optimized rotational stimulation position about the axis of the lead by: at the selected optimized longitudinal stimulation position providing stimulation at different rotational positions about the axis of the lead using the optimized stimulation waveform, recording a third evoked potential evoked by the stimulation at each of the rotational positions, and selecting the optimized rotational stimulation position based on the third evoked potential.

Also disclosed herein is a method of optimizing a position on a lead implanted in a patient's brain for providing stimulation, the lead comprising a plurality of electrodes, the method comprising: (a) determining an optimized stimulation waveform for evoking a detectable evoked potential by: using one or more of the electrodes to provide an initial stimulation waveform, determining if an evoked potential is detectable using one or more of the electrodes, if an evoked potential is not detectable, adjusting a parameter of the initial stimulation waveform until a first evoked potential is detectable, (b) determining an optimized longitudinal stimulation position along an axis of the lead by: providing stimulation at different longitudinal positions along the axis of the lead using the optimized stimulation waveform, recording a second evoked potential evoked by the stimulation at each of the longitudinal positions, and selecting the optimized longitudinal stimulation position based on the second evoked potential, and (c) determining an optimized rotational stimulation position about the axis of the lead by: at the selected optimized longitudinal stimulation position providing stimulation at different rotational positions about the axis of the lead using the optimized stimulation waveform, recording a third evoked potential evoked by the stimulation at each of the rotational positions, and selecting the optimized rotational stimulation position based on the third evoked potential. According to some embodiments, the initial stimulation waveform comprises a first phase of a first polarity, as second phase of a second polarity, and an interphase interval. According to some embodiments, adjusting a parameter of the initial stimulation waveform comprises adjusting an amplitude of the waveform. According to some embodiments, providing stimulation at different longitudinal positions comprises fractionating current among two or more of the electrodes to provide stimulation at one or more virtual electrodes that are not co-located with any of the plurality of electrodes. According to some embodiments, providing stimulation at different rotational positions comprises fractionating current among two or more directional electrodes to provide stimulation at one or more virtual electrodes that are not co-located with any of the directional electrodes. According to some embodiments, selecting the optimized longitudinal position based on the second evoked potential comprises determining values for one or more features of the second evoked potential and selecting the optimized longitudinal position based on the values. According to some embodiments, selecting the optimized rotational position based on the third evoked potential comprises determining values for one or more features of the third evoked potential and selecting the optimized longitudinal position based on the values. According to some embodiments, the method further comprises determining an indication that efficacy of therapy for the patient has declined and automatically performing the method in response to the indication. According to some embodiments, the method further comprises using the second and third evoked potentials to determine a cause of the decline in efficacy. According to some embodiments, the method further comprises determining impedances at one or more of the plurality of electrodes and using the impedances to determine a cause of the decline in efficacy. According to some embodiments, the method further comprises providing therapeutic stimulation to the patient using the determined optimized longitudinal and rotational positions, using a stimulation waveform that is different than the optimized stimulation waveform for evoking a detectable evoked potential.

Also disclosed herein is a medical device configured to optimize a position on a lead implanted in a patient's brain for providing stimulation, the lead comprising a plurality of electrodes, the device comprising: control circuitry configured to: (a) determine an optimized stimulation waveform for evoking a detectable evoked potential by: using one or more of the electrodes to provide an initial stimulation waveform, determining if an evoked potential is detectable using one or more of the electrodes, if an evoked potential is not detectable, adjusting a parameter of the initial stimulation waveform until a first evoked potential is detectable, (b) determine an optimized longitudinal stimulation position along an axis of the lead by: providing stimulation at different longitudinal positions along the axis of the lead using the optimized stimulation waveform, recording a second evoked potential evoked by the stimulation at each of the longitudinal positions, and selecting the optimized longitudinal stimulation position based on the second evoked potential, and (c) determine an optimized rotational stimulation position about the axis of the lead by: at the selected optimized longitudinal stimulation position providing stimulation at different rotational positions about the axis of the lead using the optimized stimulation waveform, recording a third evoked potential evoked by the stimulation at each of the rotational positions, and selecting the optimized rotational stimulation position based on the third evoked potential. According to some embodiments, the initial stimulation waveform comprises a first phase of a first polarity, as second phase of a second polarity, and an interphase interval. According to some embodiments, adjusting a parameter of the initial stimulation waveform comprises adjusting an amplitude of the waveform. According to some embodiments, providing stimulation at different longitudinal positions comprises fractionating current among two or more of the electrodes to provide stimulation at one or more virtual electrodes that are not co-located with any of the plurality of electrodes. According to some embodiments, providing stimulation at different rotational positions comprises fractionating current among two or more directional electrodes to provide stimulation at one or more virtual electrodes that are not co-located with any of the directional electrodes. According to some embodiments, selecting the optimized longitudinal position based on the second evoked potential comprises determining values for one or more features of the second evoked potential and selecting the optimized longitudinal position based on the values. According to some embodiments, selecting the optimized rotational position based on the third evoked potential comprises determining values for one or more features of the third evoked potential and selecting the optimized longitudinal position based on the values. According to some embodiments, the device is further configured to determine an indication that efficacy of therapy for the patient has declined and automatically performing the method in response to the indication. According to some embodiments, the device is further configured to use the second and third evoked potentials to determine a cause of the decline in efficacy. According to some embodiments, the device is further configured to determine impedances at one or more of the plurality of electrodes and using the impedances to determine a cause of the decline in efficacy. According to some embodiments, the device is further configured to provide therapeutic stimulation to the patient using the determined optimized longitudinal and rotational positions, using a stimulation waveform that is different than the optimized stimulation waveform for evoking a detectable evoked potential.

Also disclosed herein is an external device for interfacing with a medical device, wherein the medical device comprises an electrode lead configured for implantation in a patient's brain, the electrode lead comprising a plurality of electrodes configurable to provide electrical stimulation to the patient's brain and to record electrical signals, wherein the external device comprises: control circuitry configured to: render a graphical user interface (GUI) configured to: display a plot indicative of electrical signals recorded at one or more of the electrodes, allow a user to select a portion of the plot and save the selected portion as a first template, and overlay one or more second templates with the plot. According to some embodiments, the one or more second templates are templates that were previously saved using the GUI. According to some embodiments, the one or more second templates are templates provided in a template library of the GUI. According to some embodiments, the GUI is configured to allow a user to define a portion of the plot as baseline signal. According to some embodiments, the GUI is configured to subtract the defined baseline signal from subsequently displayed plots. According to some embodiments, the GUI is configured to display an indication of the defined baseline signal on subsequently displayed plots. According to some embodiments, the GUI is configured to allow a user to define a portion of the plot as a stimulation artifact. According to some embodiments, the GUI is configured to subtract the defined stimulation artifact from subsequently displayed plots. According to some embodiments, the plot indicative of electrical signals recorded at one or more of the electrodes comprises time-aligned average signals from a plurality of stimulation epochs. According to some embodiments, the plot indicative of electrical signals recorded at one or more of the electrodes comprises a time domain plot. According to some embodiments, the plot indicative of electrical signals recorded at one or more of the electrodes comprises a frequency domain plot. According to some embodiments, wherein the GUI is configured to automatically identify features of evoked potentials from the plot. According to some embodiments, the features are selected maxima and/or minima. According to some embodiments, wherein the GUI is configured to identify regions of the plot corresponding to known neurological signals. According to some embodiments, wherein the GUI is configured to identify features of the plot corresponding to known indicators of noise and/or interference. According to some embodiments, wherein the GUI is configured to automatically remove the noise and/or interference from the plot.

Also disclosed herein is a method for assisting a user to optimize an electrode lead configuration for providing deep brain stimulation (DBS) for a patient using an electrode lead implantable in the patient's brain, wherein the electrode lead comprises a plurality of electrode contacts, the method comprising: receiving parameters specifying a first stimulation location on the lead at which to provide stimulation, wherein the first stimulation location was previously determined using a first lead optimization algorithm, receiving a first one or more values for one or more features extracted from recorded first evoked potentials (EPs) that were previously determined during the first lead optimization algorithm, providing stimulation to the patient using the first stimulation location and recording second EPs evoked by the stimulation, extracting a second one or more values for the one or more features from the second EPs, and comparing the first and second one or more values to determine if the lead has moved since the first lead optimization algorithm was performed. According to some embodiments, the first and second EPs each comprise evoked resonant neural activity. According to some embodiments, comparing the first and second one or more values comprises determining a difference between the first and second one or more values. According to some embodiments, determining an indication of lead movement comprises comparing the difference to a predetermined threshold value. According to some embodiments, the method further comprises causing a user interface to display an indication that the lead has moved if the difference exceeds the threshold value. According to some embodiments, the method further comprises using the indication of lead movement to determine whether to use the first stimulation location as an input for a second lead optimization algorithm. According to some embodiments, the method comprises determining not to use the first stimulation location as an input for a second lead optimization algorithm if the difference exceeds the threshold value. According to some embodiments, the method further comprises performing the second algorithm using a second stimulation location that is different than the first pole configuration. According to some embodiments, the method further comprises performing the first lead optimization algorithm. According to some embodiments, the first lead optimization algorithm comprises a lead implantation algorithm configured to assist a user to implant the one or more electrode leads in the patient's brain. According to some embodiments, the second lead optimization algorithm is configured to optimize a location on the electrode lead for providing stimulation. According to some embodiments, determining if the lead has moved comprises determining if the lead has moved longitudinally. According to some embodiments, the method further comprises determining a distance the lead has moved longitudinally. According to some embodiments, determining if the lead has moved comprises determining if the lead has rotated. According to some embodiments, the method further comprises determining a degree to which the lead has rotated. According to some embodiments, According to some embodiments, the method further comprises determining a second stimulation location that compensates for any determined lead movement. According to some embodiments, the second stimulation location is configured to evoke third EPs having third values for the one or more extracted features that differ from the first values by less than a predetermined threshold value. According to some embodiments, the method further comprises confirming that the third values differ from the first values by less than the predetermined threshold value.

Also disclosed herein is a system for optimizing a stimulation lead implanted in a patient's brain, the lead comprising a plurality of electrodes, the system comprising: a graphical user interface, and control circuitry configured to: receive parameters specifying a first stimulation location on the lead at which to provide stimulation, wherein the first stimulation location was previously determined using a first lead optimization algorithm, receive a first one or more values for one or more features extracted from recorded first evoked potentials (EPs) that were previously determined during the first lead optimization algorithm, cause stimulation circuitry to provide stimulation to the patient using the first stimulation location and record second EPs evoked by the stimulation, extract a second one or more values for the one or more features from the second EPs, and compare the first and second one or more values to determine if the lead has moved since the first lead optimization algorithm was performed. According to some embodiments, the first and second EPs each comprise evoked resonant neural activity. According to some embodiments, comparing the first and second one or more values comprises determining a difference between the first and second one or more values. According to some embodiments, determining an indication of lead movement comprises comparing the difference to a predetermined threshold value. According to some embodiments, the control circuitry is further configured to cause the user interface to display an indication that the lead has moved if the difference exceeds the threshold value. According to some embodiments, the control circuitry is further configured to use the indication of lead movement to determine whether to use the first stimulation location as an input for a second lead optimization algorithm. According to some embodiments, the control circuitry is configured to not use the first stimulation location as an input for a second lead optimization algorithm if the difference exceeds the threshold value. According to some embodiments, the control circuitry is further configured to perform the second algorithm using a second stimulation location that is different than the first pole configuration. According to some embodiments, the control circuitry is further configured to perform the first lead optimization algorithm. According to some embodiments, the first lead optimization algorithm comprises a lead implantation algorithm configured to assist a user to implant the one or more electrode leads in the patient's brain. According to some embodiments, the second lead optimization algorithm is configured to optimize a location on the electrode lead for providing stimulation. According to some embodiments, determining if the lead has moved comprises determining if the lead has moved longitudinally. According to some embodiments, the control circuitry is further configured to determine a distance the lead has moved longitudinally. According to some embodiments, determining if the lead has moved comprises determining if the lead has rotated. According to some embodiments, the control circuitry is further configured to determine a degree to which the lead has rotated. According to some embodiments, the control circuitry is further configured to determine a second stimulation location that compensates for any determined lead movement. According to some embodiments, the second stimulation location is configured to evoke third EPs having third values for the one or more extracted features that differ from the first values by less than a predetermined threshold value. According to some embodiments, the control circuitry is further configured to confirm that the third values differ from the first values by less than the predetermined threshold value.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS. The invention may also reside in one or more non-transitory computer-readable media comprising instructions, which when executed by a processor of a machine configure the machine to perform any of the above methods.

DETAILED DESCRIPTION

Figure 1A:
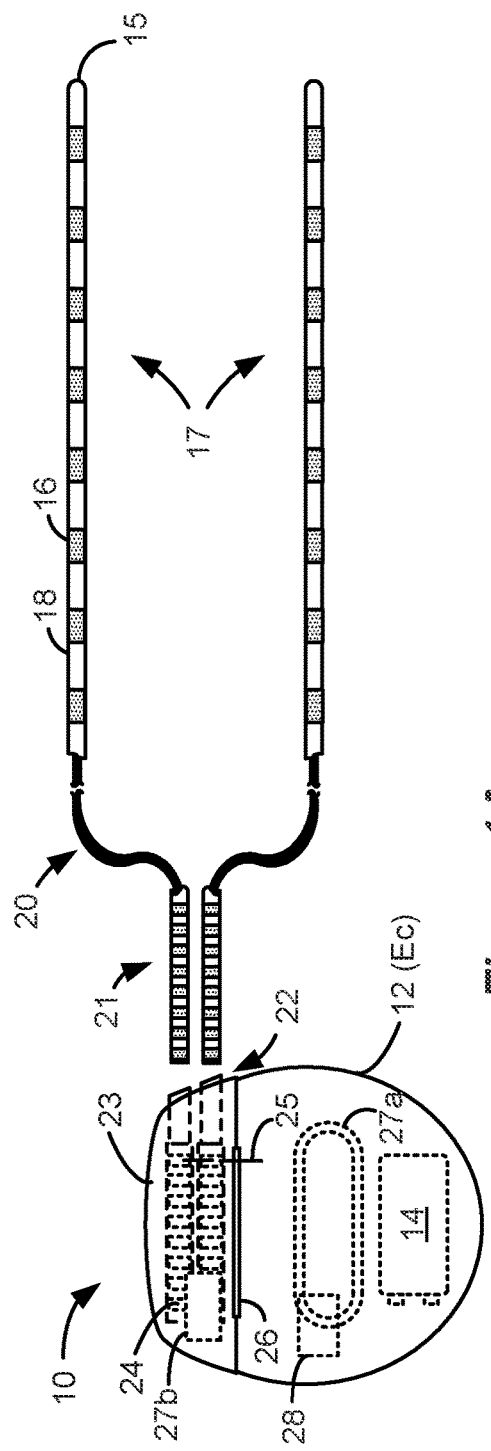
FIG. 1A shows an Implantable Pulse Generator (IPG).

An implantable neurostimulator system, such as a DBS system, typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more electrode leads 15 can be used having ring-shaped electrodes 16 carried on a flexible body 18.

Figure 1B:
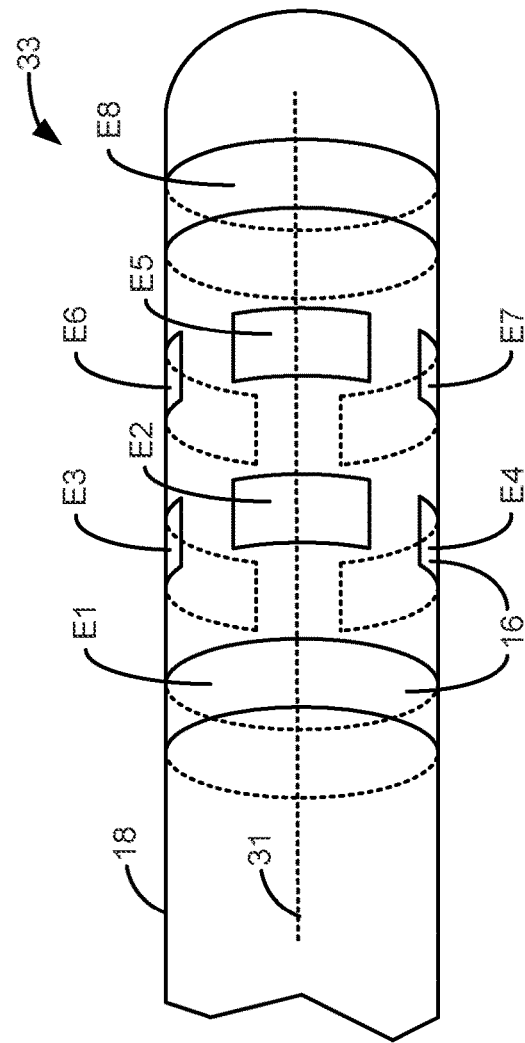
FIG. 1B shows a percutaneous lead having split-ring electrodes.

In yet another example shown in FIG. 1B, an electrode lead 33 can include one or more split-ring electrodes. In this example, eight electrodes 16 (E1-E8) are shown, though the number of electrodes may vary. Electrode E8 at the distal end of the lead and electrode E1 at a proximal end of the lead comprise ring electrodes spanning 360 degrees around a central axis of the lead 33. Electrodes E2, E3, and E4 comprise split-ring electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring electrodes, but are located at a different longitudinal position along the central axis 31 than are split ring electrodes E2, E3, and E4. As shown, the split-ring electrodes E2-E4 and E5-E7 may be located at longitudinal positions along the axis 31 between ring electrodes E1 and E8. However, this is just one example of a lead 33 having split-ring electrodes. In other designs, all electrodes can be split-ring, or there could be different numbers of split-ring electrodes at each longitudinal position (i.e., more or less than three), or the ring and split-ring electrodes could occur at different or random longitudinal positions, etc.

Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are sixteen electrodes (E1-E16), split between two percutaneous leads 15 (or contained on a single paddle lead, not shown) and thus the header 23 may include a 2×2 array of eight-electrode lead connectors 22. However, the type and number of leads, and the number of electrodes, in an IPG is application specific and therefore can vary. The conductive case 12 can also comprise an electrode (Ec).

In a DBS application, as is useful in the treatment of movement symptoms in Parkinson's disease for example, the IPG 10 is typically implanted under the patient's clavicle (collarbone). Lead wires 20 are tunneled through the neck and the scalp and the electrode leads 15 (or 33) are implanted through holes drilled in the skull and positioned for example in the subthalamic nucleus (STN) and the Globus pallidus internus (GPi) in each brain hemisphere.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1A, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Bluetooth Low Energy (BLE), as described in U.S. Patent Publication 2019/0209851, Zigbee, WiFi, MICS, and the like.

Figure 2A:
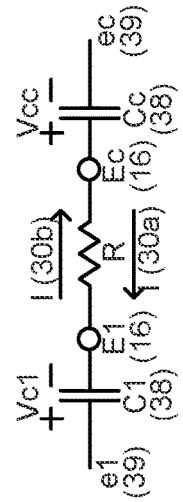
FIGS. 2A and 2B show an example of stimulation pulses (waveforms) producible by the IPG or by an External Trial Stimulator (ETS).

Stimulation in IPG 10 is typically provided by electrical pulses each of which may include a number of phases such as 30a and 30b, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30a), and thus provides pulses which sink a negative current of amplitude −I from the tissue. The case electrode Ec has been selected as an anode (again during first phase 30a), and thus provides pulses which source a corresponding positive current of amplitude +I to the tissue. Note that at any time the current sunk from the tissue (e.g., −I at E1 during phase 30a) equals the current sourced to the tissue (e.g., +I at Ec during phase 30a) to ensure that the net current injected into the tissue is zero. The polarity of the currents at these electrodes can be changed: Ec can be selected as a cathode, and E1 can be selected as an anode, etc.

Figure 3:
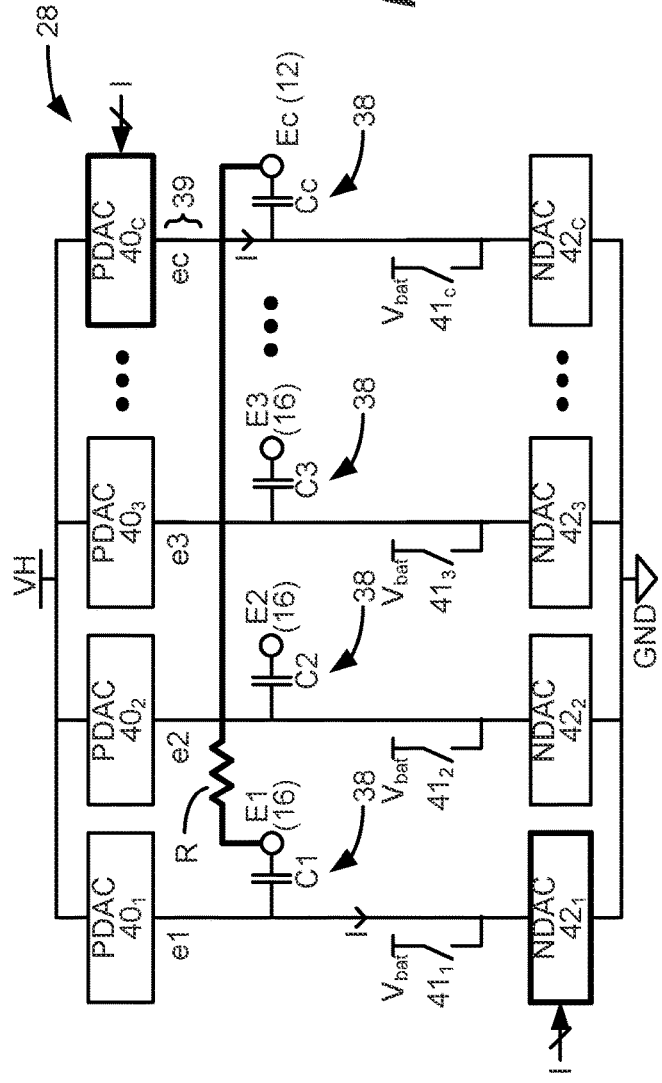
FIG. 3 shows an example of stimulation circuitry useable in the IPG or ETS.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node Ei 39. Each electrode node Ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first pulse phase 30a of FIG. 2A, electrode E1 has been selected as a cathode electrode to sink current from the tissue R and case electrode Ec has been selected as an anode electrode to source current to the tissue R. Thus, PDAC $40_C$ and NDAC $42_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796. The stimulation circuitries described herein provide multiple independent current control (MICC) (or multiple independent voltage control) to guide the estimate of current fractionalization among multiple electrodes and estimate a total amplitude that provides a desired strength. In other words, the total anodic current can be split among two or more electrodes and/or the total cathodic current can be split among two or more electrodes, allowing the stimulation location and resulting field shapes to be adjusted. For example, a "virtual electrode" may be created at a position between two physical electrodes by fractionating current between the two electrodes. In other words, the virtual electrode is not co-located with any of the physical electrodes. Appreciate, that in the context of split ring electrodes, such as electrodes E2-E4 (FIG. 1B), current fractionating can be used to create a virtual electrode at a rotational angle that is between two physical split ring electrodes (e.g., between E2 and E3). Accordingly, current fractionalization can be used to provide stimulation at any location along the lead and at any rotational angle about the lead. Note also that split ring electrodes at a given longitudinal position on the lead can be "ganged" together to effectively create a ring electrode at that position. As used herein, the term "pole configuration" may refer to which electrodes are active at a given time and how current is proportioned among the active electrodes. The pole configuration specifies the location upon the lead at which stimulation is provided.

Much of the stimulation circuitry 28 of FIG. 3, including the PDACs $40_i$ and NDACs $42_i$ the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Figure 2B:
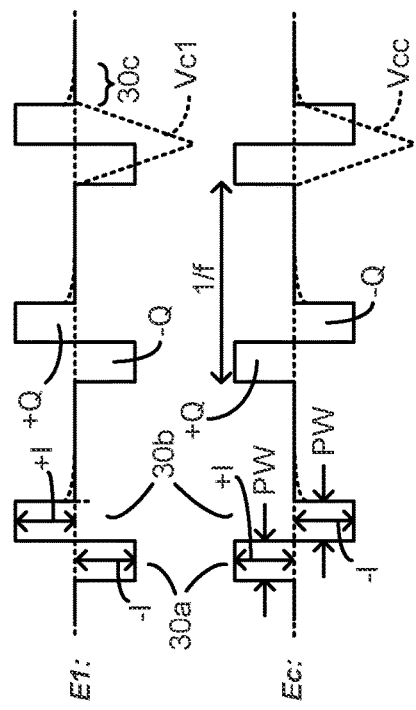

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will build up across the DC-blockings capacitors C1 and Cc associated with the electrodes E1 and Ec used to produce the current, giving rise to voltages Vc1 and Vcc which decrease in accordance with the amplitude of the current and the capacitance of the capacitors 38 (dV/dt=I/C). During the second pulse phase 30*b*, when the polarity of the current I is reversed at the selected electrodes E1 and Ec, the stored charge on capacitors C1 and Cc is actively recovered, and thus voltages Vc1 and Vcc increase and return to 0V at the end the second pulse phase 30*b*.

To recover all charge by the end of the second pulse phase 30*b* of each pulse (Vc1=Vcc=0V), the first and second phases 30*a* and 30*b* are charged balanced at each electrode, with the first pulse phase 30*a* providing a charge of –Q (–I*PW) and the second pulse phase 30*b* providing a charge of +Q (+I*PW) at electrode E1, and with the first pulse phase 30*a* providing a charge of +Q and the second pulse phase 30*b* providing a charge of –Q at the case electrode Ec. In the example shown, such charge balancing is achieved by using the same pulse width (PW) and the same amplitude (III) for each of the opposite-polarity pulse phases 30*a* and 30*b*. However, the pulse phases 30*a* and 30*b* may also be charged balance at each electrode if the product of the amplitude and pulse widths of the two phases 30*a* and 30*b* are equal, or if the area under each of the phases is equal, as is known.

FIG. 3 shows that stimulation circuitry 28 can include passive recovery switches 41$_i$, which are described further in U.S. Patent Application Publications 2018/0071527 and 2018/0140831. Passive recovery switches 41$_i$ may be attached to each of the electrode nodes ei 39, and are used to passively recover any charge remaining on the DC-blocking capacitors Ci 38 after issuance of the second pulse phase 30*b*—i.e., to recover charge without actively driving a current using the DAC circuitry. Passive charge recovery can be prudent, because non-idealities in the stimulation circuitry 28 may lead to pulse phases 30*a* and 30*b* that are not perfectly charge balanced.

Therefore, and as shown in FIG. 2A, passive charge recovery typically occurs after the issuance of second pulse phases 30*b*, for example during at least a portion 30*c* of the quiet periods between the pulses, by closing passive recovery switches 41$_i$. As shown in FIG. 3, the other end of the switches 41$_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially decaying curves during 30*c* in FIG. 2A, which may be positive or negative depending on whether pulse phase 30*a* or 30*b* have a predominance of charge at a given electrode.

Passive charge recovery 30*c* may alleviate the need to use biphasic pulses for charge recovery, especially in the DBS context when the amplitudes of currents may be lower, and therefore charge recovery less of a concern. For example, and although not shown in FIG. 2A, the pulses provided to the tissue may be monophasic, comprising only a first pulse phase 30*a*. This may be followed thereafter by passive charge recovery 30*c* to eliminate any charge build up that occurred during the singular pulses 30*a*.

Figure 4:
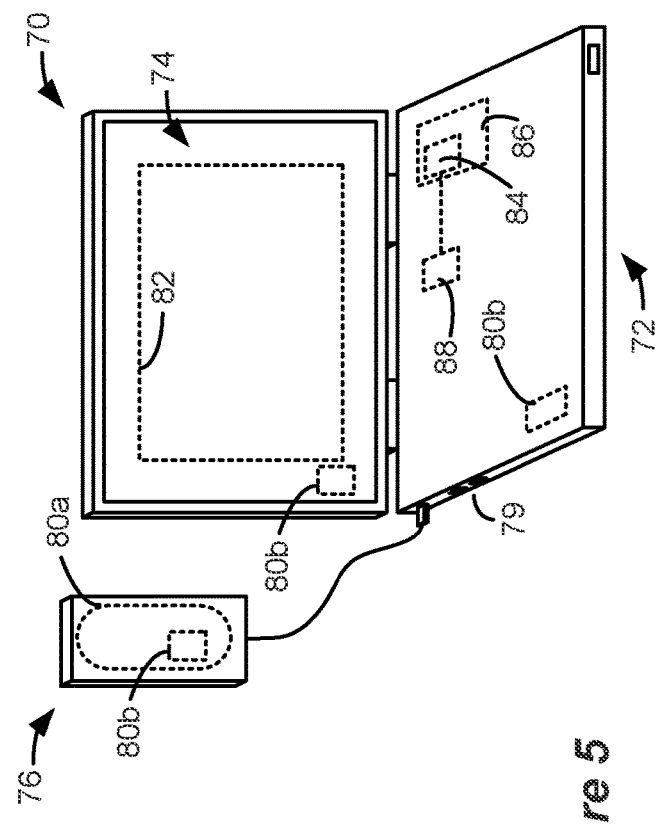
FIG. 4 shows an ETS environment useable to provide stimulation before implantation of an IPG.

FIG. 4 shows an external trial stimulation (ETS) that may be used prior to implantation of an IPG 10 in a patient, for example, in the operating room to test stimulation and confirm the lead position. During external trial stimulation, stimulation can be tried on the implant patient to evaluate therapeutic and side-effect thresholds and confirm that the lead is not too close to structures that cause side effects. Note that the term ETS, as used herein, refers broadly to any non-implanted device used to control the implanted leads to deliver stimulation, whether during the surgical implantation of the leads, during a fitting/programming session, etc. Like the IPG 10, the ETS 50 can include one or more antennas to enable bi-directional communications with external devices such as those shown in FIG. 5. Such antennas can include a near-field magnetic-induction coil antenna 56*a*, and/or a far-field RF antenna 56*b*, as described earlier. ETS 50 may also include stimulation circuitry able to form stimulation in accordance with a stimulation program, which circuitry may be similar to or comprise the same stimulation circuitry 28 (FIG. 3) present in the IPG 10. ETS 50 may also include a battery (not shown) for operational power. The sensing capabilities described herein with regard to the IPG 10, may also be included in the ETS for the purposes described below. As the IPG may include a case electrode, an ETS may provide one or more connections to establish similar returns; for example, using patch electrodes. Likewise, the ETS may communicate with the clinician programmer (CP) 70 so that the CP can process the data as described below.

Figure 5:
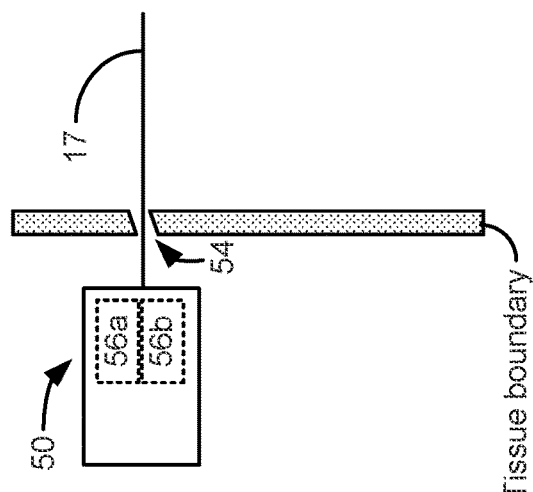
FIG. 5 shows various external devices capable of communicating with and programming stimulation in an IPG or ETS.
Figure 5:
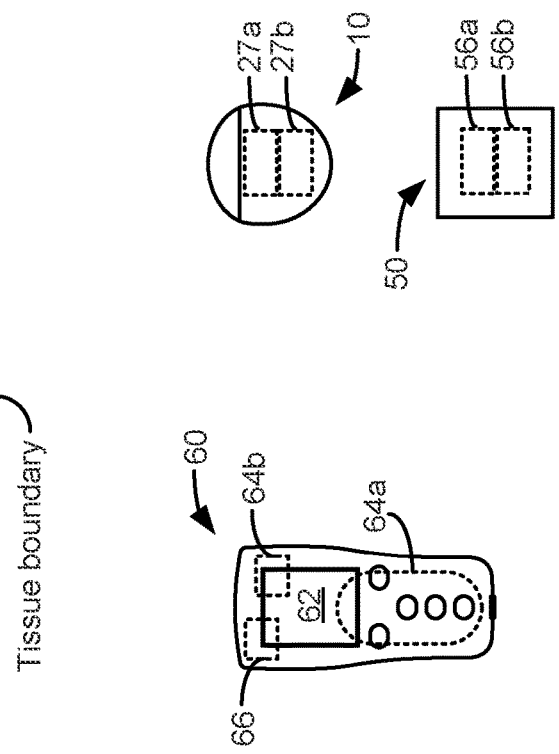

FIG. 5 shows various external devices that can wirelessly communicate data with the IPG 10 or ETS 50, including a patient hand-held external controller 60, and a clinician programmer (CP) 70. Both of devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS such as various status information, etc.

External controller 60 can be as described in U.S. Patent Application Publication 2015/0080982 for example and may comprise a controller dedicated to work with the IPG 10 or ETS 50. External controller 60 may also comprise a general-purpose mobile electronics device such as a mobile phone, tablet, or other computing device that has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64*a* capable of wirelessly communicating with the coil antenna 27*a* or 56*a* in the IPG 10 or ETS 50. The external controller 60 can also have a far-field RF antenna 64*b* capable of wirelessly communicating with the RF antenna 27*b* or 56*b* in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS can depend on the type of antennas included in those devices. If the patient's IPG 10 or ETS includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas or 80b to communicate stimulation parameters chosen through the GUI 82 to the patient's IPG 10.

The user interface of the external controller 60 may provide similar functionality because the external controller 60 can include similar hardware and software programming as the clinician programmer. For example, the external controller 60 includes control circuitry 66 similar to the control circuitry 88 in the clinician programmer 70 and may similarly be programmed with external controller software stored in device memory.

Figure 6:
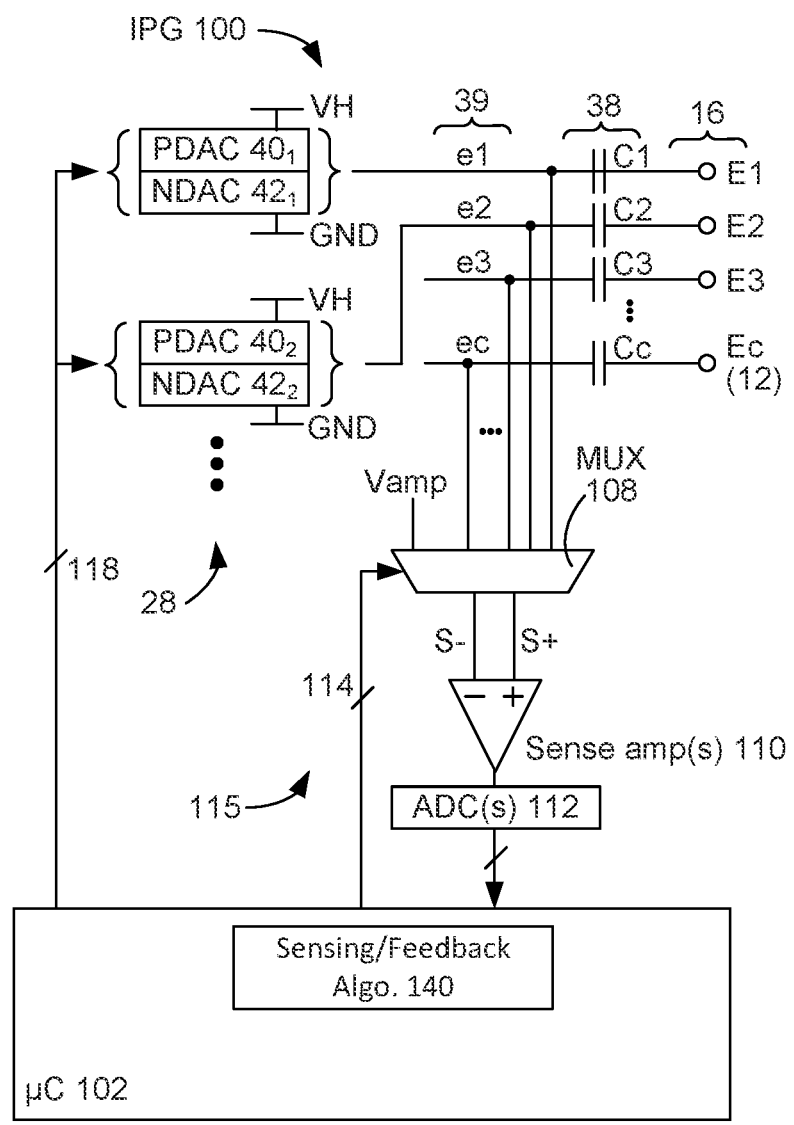
FIG. 6 illustrates sensing circuitry useable in an IPG.

An increasingly interesting development in pulse generator systems is the addition of sensing capability to complement the stimulation that such systems provide. FIG. 6 shows an IPG 100 that includes stimulation and sensing functionality. (An ETS as described earlier could also include stimulation and sensing capabilities). FIG. 6 shows further details of the circuitry in an IPG 100 that can provide stimulation and sensing spontaneous or evoked signals. The IPG 100 includes control circuitry 102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier. The control circuitry 102 may be configured with one or more sensing/feedback algorithms 140 that are configured to cause the IPG to make certain adjustments and/or take certain actions based on the sensed neural signals.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 to one or more PDACs $40_i$ or NDACs $42_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present but are not shown in FIG. 6 for simplicity.

IPG 100 also includes sensing circuitry 115, and one or more of the electrodes 16 can be used to sense spontaneous or evoked electrical signals, e.g., bi ° potential s from the patient's tissue. In this regard, each electrode node 39 can further be coupled to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 6, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the signals being sensed will still readily be sensed by the sense amp circuitry 110. In other examples, signals may be sensed directly at the electrodes 16 without passage through intervening capacitors 38.

According to some embodiments, it may be preferred to sense signals differentially, and in this regard, the sense amp circuitry 110 comprises a differential amplifier receiving the sensed signal S+ (e.g., E3) at its non-inverting input and the sensing reference S− (e.g., E1) at its inverting input. As one skilled in the art understands, the differential amplifier will subtract S− from S+ at its output, and so will cancel out any common mode voltage from both inputs. This can be useful for example when sensing various neural signals, as it may be useful to subtract the relatively large-scale stimulation artifact from the measurement (as much as possible). Examples of sense amp circuitry 110, and manner in which such circuitry can be used, can be found in U.S. Patent Application Publications 2019/0299006, 2020/0305744, 2020/0305745 and 2022/0233866. The IPG (and/or ETS) may also be configured to determine impedances at any of the electrodes. For example, the IPG (and/or ETS) may be configured with sample and hold circuitry, controlled by the control circuitry for measuring impedances.

Figure 7:
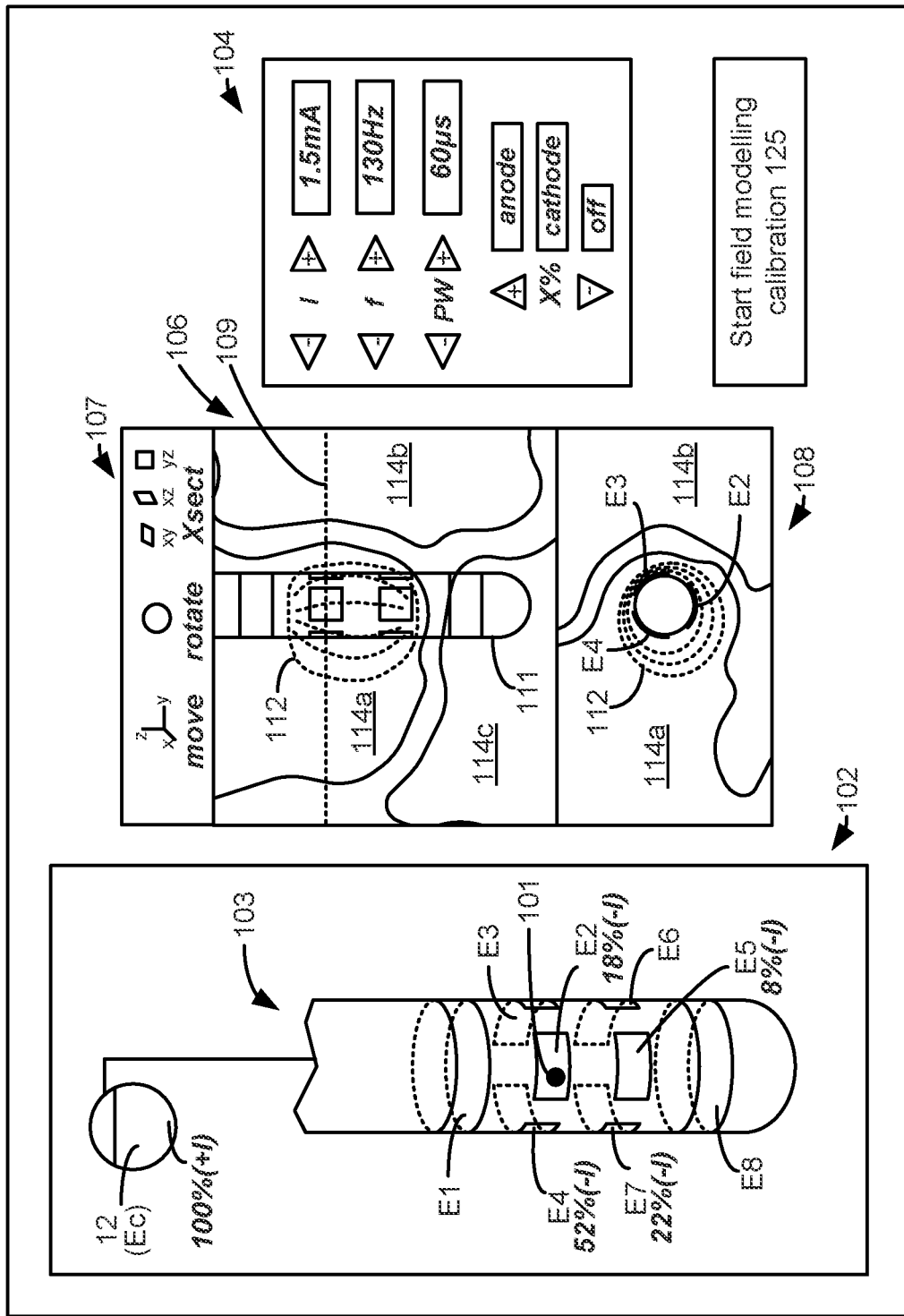
FIG. 7 illustrates an embodiment of a user interface (UI) for programming stimulation.

Particularly in the DBS context, it can be useful to provide a clinician with a visual indication of how stimulation selected for a patient will interact with the tissue in which the electrodes are implanted. This is illustrated in FIG. 7, which shows a Graphical User Interface (GUI) 100 operable on an external device capable of communicating with an IPG 110 or ETS 150. Typically, and as assumed in the description that follows, GUI 100 would be rendered on a clinician programmer 70 (FIG. 5), which may be used during surgical implantation of the leads, or after implantation when a therapeutically useful stimulation program is being chosen for a patient. However, GUI 100 could be rendered on a patient external programmer 60 (FIG. 5) or any other external device capable of communicating with the IPG 110 or ETS 150.

GUI 100 allows a clinician (or patient) to select the stimulation program that the IPG 110 or ETS 150 will provide and provides options that control sensing of spontaneous or evoked responses, as described below. In this regard, the GUI 100 may include a stimulation parameter interface 104 where various aspects of the stimulation program can be selected or adjusted. For example, interface 104 allows a user to select the amplitude (e.g., a current I) for stimulation; the frequency (f) of stimulation pulses; and the pulse width (PW) of the stimulation pulses. Stimulation parameter interface 104 can be significantly more complicated, particularly if the IPG 100 or ETS 150 supports the provision of stimulation that is more complicated than a repeating sequence of pulses. See, e.g., U.S. Patent Application Publication 2018/0071513. Nonetheless, interface 104 is simply shown for simplicity in FIG. 7 as allowing only for amplitude, frequency, and pulse width adjustment. Stimulation parameter interface 104 may include inputs to allow a user to select whether stimulation will be provided using biphasic (FIG. 2A) or monophasic pulses, and to select whether passive charge recovery will be used, although again these details aren't shown for simplicity.

Stimulation parameter interface 104 may further allow a user to select the active electrodes—i.e., the electrodes that will receive the prescribed pulses. Selection of the active electrodes can occur in conjunction with a leads interface 102, which can include an image 103 of the one or more leads that have been implanted in the patient. Although not shown, the leads interface 102 can include a selection to access a library of relevant images 103 of the types of leads that may be implanted in different patients.

In the example shown in FIG. 7, the leads interface 102 shows an image 103 of a single split-ring lead 33 like that described earlier with respect to FIG. 1B. The leads interface 102 can include a cursor 101 that the user can move (e.g., using a mouse connected to the clinician programmer 70) to select an illustrated electrode 16 (e.g., E1-E8, or the case electrode Ec). Once an electrode has been selected, the stimulation parameter interface 104 can be used to designate the selected electrode as an anode that will source current to the tissue, or as a cathode that will sink current from the tissue. Further, the stimulation parameter interface 104 allows the amount of the total anodic or cathodic current +I or −I that each selected electrode will receive to be specified in terms of a percentage, X. For example, in FIG. 7, the case electrode 12 Ec is specified to receive X=100% of the current I as an anodic current +I. The corresponding cathodic current −I is split between electrodes E2 (0.18*−I), E4 (0.52*−I), E5 (0.08*−I), and E7 (0.22*−I). Thus, two or more electrodes can be chosen to act as anodes or cathodes at a given time using MICC (as described above), allowing the electric field in the tissue to be shaped. The currents so specified at the selected electrodes can be those provided during a first pulse phase (if biphasic pulses are used), or during an only pulse phase (if monophasic pulses are used).

GUI 100 can further include a visualization interface 106 that can allow a user to view an indication of the effects of stimulation, such as electric field image 112 formed on the one or more leads given the selected stimulation parameters. The electric field image 112 is formed by field modelling in the clinician programmer 70. Only one lead is shown in the visualization interface 106 for simplicity, although again a given patient might be implanted with more than one lead. Visualization interface 106 provides an image 111 of the lead(s) which may be three-dimensional.

The visualization interface 106 preferably, but not necessarily, further includes tissue imaging information 114 taken from the patient, represented as three different tissue structures 114a, 114b and 114c in FIG. 7 for the patient in question, which tissue structures may comprise different areas of the brain for example. Such tissue imaging information may comprise a Magnetic Resonance Image (MRI), a Computed Tomography (CT) image or other type of image and is preferably taken prior to implantation of the lead(s) in the patient. Often, one or more images, such as an MRI, CT, and/or a brain atlas are scaled and combined in a single image model. As one skilled in the art will understand, the location of the lead(s) can be precisely referenced to the tissue structures 114i because the lead(s) are implanted using a stereotactic frame (not shown). This allows the clinician programmer 70 on which GUI 100 is rendered to overlay the lead image 111 and the electric field image 112 with the tissue imaging information in the visualization interface 106 so that the position of the electric field 112 relative to the various tissue structures 114i can be visualized. The image of the patient's tissue may also be taken after implantation of the lead(s), or tissue imaging information may comprise a generic image pulled from a library which is not specific to the patient in question.

The various images shown in the visualization interface 106 (i.e., the lead image 111, the electric field image 112, and the tissue structures 114i) can be three-dimensional in nature, and hence may be rendered in the visualization interface 106 in a manner to allow such three-dimensionality to be better appreciated by the user, such as by shading or coloring the images, etc. Additionally, a view adjustment interface 107 may allow the user to move or rotate the images, using cursor 101 for example.

GUI 100 can further include a cross-section interface 108 to allow the various images to be seen in a two-dimensional cross section. Specifically, cross-section interface 108 shows a particular cross section 109 taken perpendicularly to the lead image 111 and through split-ring electrodes E2, E3, and E4. This cross section 109 can also be shown in the visualization interface 106, and the view adjustment interface 107 can include controls to allow the user to specify the plane of the cross section 109 (e.g., in XY, XZ, or YZ planes) and to move its location in the image. Once the location and orientation of the cross section 109 is defined, the cross-section interface 108 can show additional details. For example, the electric field image 112 can show equipotential lines allowing the user to get a sense of the strength and reach of the electric field at different locations. Although GUI 100 includes stimulation definition (102, 104) and imaging (108, 106) in a single screen of the GUI, these aspects can also be separated as part of the GUI 100 and made accessible through various menu selections, etc.

Figure 8:
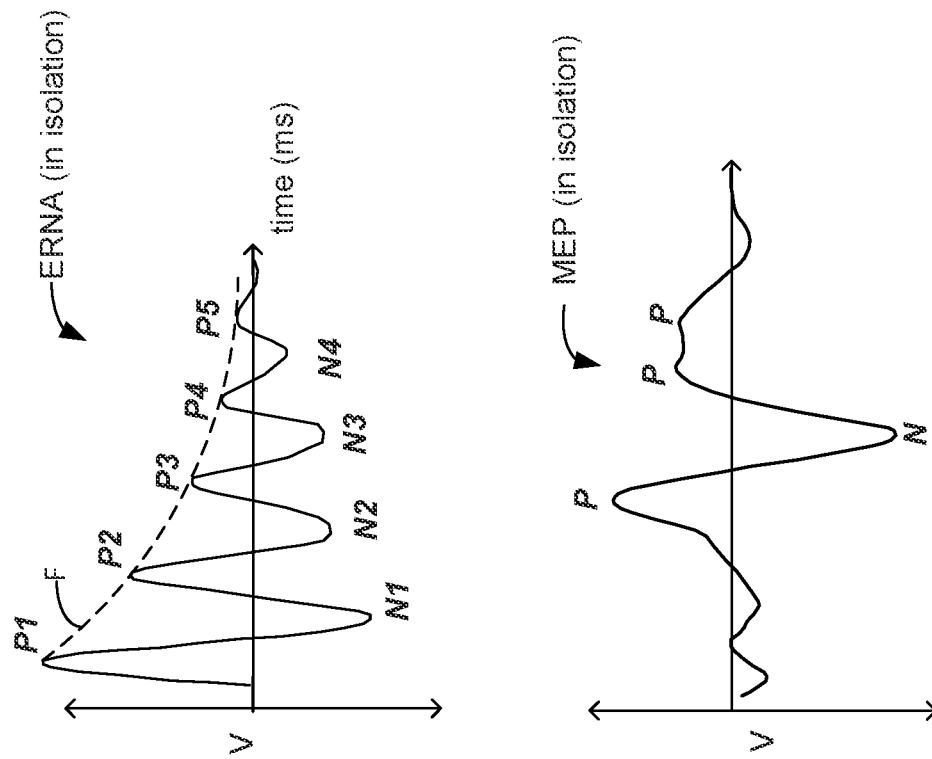
FIG. 8 illustrates examples of evoked potentials.

It has been observed that DBS stimulation in certain positions in the brain can evoke neural responses, i.e., electrical activity from neural elements, which may be measured. Such evoked neural responses are referred to herein generally as evoked potentials (EPs). One example of such neural responses are resonant neural responses, referred to herein as evoked resonant neural responses (ERNAs). See, e.g., Sinclair, et al., "Subthalamic Nucleus Deep Brain Stimulation Evokes Resonant Neural Activity," Ann. Neurol. 83(5), 1027-31, 2018. The ERNA responses typically have an oscillation frequency of about 200 to about 500 Hz. Stimulation of the STN, and particularly of the dorsal subregion of the STN, has been observed to evoke strong ERNA responses, whereas stimulation of the posterior subthalamic area (PSA) does not evoke such responses. Thus, ERNA may provide a biomarker for electrode location, which can indicate acceptable or optimal lead placement and/or stimulation field placement for achieving the desired therapeutic response. An example of an ERNA in isolation is illustrated in FIG. 8. The ERNA comprises a number of positive peaks $P_n$, and negative peaks $N_n$, which may have characteristic amplitudes, separations, or latencies. The ERNA signal may decay according to a characteristic decay function F. Such characteristics of the ERNA response may provide indications of the brain activity associated with the neural response.

Another example of an evoked potentials are motor evoked potentials (MEPs), which are electrical signals recorded from the descending motor pathways or from muscles following stimulation of motor pathways in the brain. An MEP is shown in isolation in FIG. 8, and comprises a number of peaks that are conventionally labeled with P for positive peaks and N for negative peaks. Note that not all MEPs will have the exact shape and number of peaks as illustrated in FIG. 8. Other examples of electrical activity that may be recorded include spontaneous neural activity (local field potentials) as well as other evoked potentials, such as cortical evoked potentials, compound muscle action potentials (CMAPs), evoked compound action potentials (ECAPs), and the like.

Aspects of this disclosure particularly relate to methods and systems for using evoked potentials, such as ERNA, MEPs and other evoked potentials, as well as other recorded electrical signals, such as local field potentials and/or spontaneous activity, to inform aspects of neuromodulation therapy, such as DBS therapy. The recorded electrical activity can be combined with other electrical measurements, such as impedance measurements. The measurements described herein can be used during the surgical implantation of the electrode leads to help the clinician implant the lead in the desired location within the patient's brain. As described in more detail below, the clinician may obtain measurements as a function of depth as they advance the lead from the entry point of the brain along the trajectory to the desired neural target to create a spatial profile of the evoked potentials along the trajectory. Once the clinician has determined that the lead is at an optimal location with respect to the target neural tissue, the methods and systems described herein can be used to determine the optimal stimulation location, with respect to both the longitudinal position along the lead and the angular position about the lead (using directional electrodes). MICC and current fractionalization can be used to provide center points of stimulation that are between physical electrodes. The recorded evoked potentials and other electrical signals can also be used during fitting to facilitate determining optimal stimulation parameters for providing therapy. The recorded evoked potentials and other electrical signals determined during implantation and/or during fitting can be stored and used for feedback control of stimulation parameters and for tracking changes in the patient's therapy over time. The disclosure also relates to providing the user, such as a clinician with a graphical user interface (GUI) to facilitate the various methods and workflows described herein.

Figure 9A:
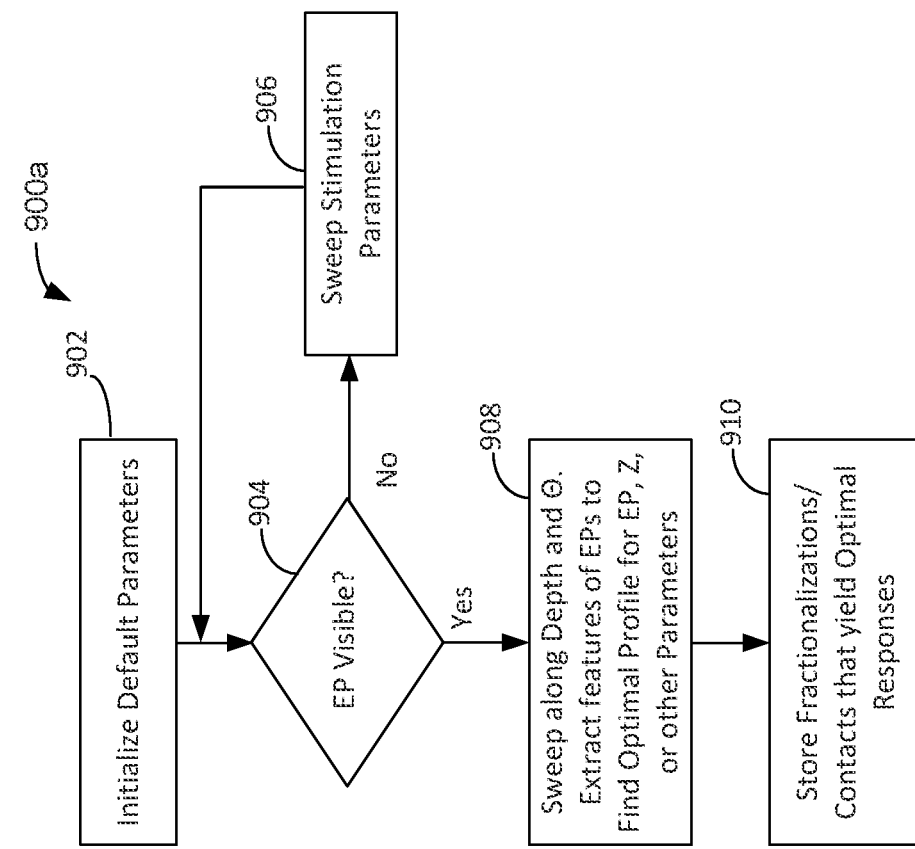
FIG. 9A illustrates a workflow for determining an optimal position on a lead for providing stimulation to a neural target and for identifying optimal stimulation parameters.

FIG. 9A illustrates an example of a workflow 900a for determining optimal contacts and/or current fractionalizations for providing stimulation to a patient. In other words, the workflow 900a may determine the optimal location ("the sweet spot") upon the electrode lead for providing stimulation. Such algorithms may be referred to herein as "sweet spot algorithms." Parameters and features recorded during the workflow 900a may also be saved, for example, to provide one or more feedback variables for closed loop control of the patient's stimulation and/or for tracking the efficacy of the patient's therapy over time. In the context of the workflow illustrated in FIG. 9A, assume that an electrode lead comprising ring electrodes and directional electrodes (e.g., electrode lead 33, FIG. 1B) has been implanted in the patient's brain proximate to one or more target neural elements. As explained in more detail below, the disclosed methods and systems can be used to facilitate such implantation (e.g., FIG. 9B), but here, assume that the lead is already at the final location.

At step 902, a set of default stimulation parameters can be initialized. The default stimulation parameters may correspond to stimulation parameters that are appropriate for therapeutic stimulation or the default parameters may be configured specifically for the evoked potential sensing workflow. For example, according to some embodiments, the default stimulation parameters optimized for sensing may comprise stimulation waveforms having active recharge (i.e., biphasic pulses) having short pulse widths (e.g., 50 µs or less) and comprising a long interphase interval (e.g., an interphase interval of 3 ms or greater). With such waveforms, the evoked potentials and other electrical measurements may be recorded during the interphase interval. Alternatively, the interphase interval could be shortened, and the recording can be conducted after the pulses. Still alternatively, monophasic pulses could be used. According to some embodiments, one or more bursts or envelopes of a plurality of pulse (e.g., ten pulses) may be used.

At step 904, one or more of the electrodes on the lead are used as sensing/recording electrodes to check for the presence of evoked potentials. According to some embodiments, all of the electrodes that are not being used to provide the stimulation are used as sensing/recording electrodes. According to some embodiments, electrodes on different leads from the stimulating electrode may be used for recording. Also note that spontaneous activity may be recorded without the need to stimulate. According to some embodiments, directional electrodes at a given longitudinal position on the lead are ganged together to function as a ring electrode for stimulation and/or sensing. If evoked potentials are not detected at one or more of the sensing/recording electrodes, the stimulation parameters may be modified (i.e., swept) to provide stimulation that evokes detectable response potentials (step 906). For example, the amplitude of the stimulation waveform may be increased.

Once it is determined that the stimulation is providing usable evoked potentials, the stimulation may be swept along the longitudinal and angular (i.e., rotational) positions on the lead to determine the optimum stimulation location (step 908). For example, for the longitudinal sweep the electrode contacts at each longitudinal position can iteratively be used as the stimulating electrode and the other electrode contacts can be used as sensing/recording electrodes. Again, directional electrodes at a given longitudinal location on the lead can be ganged together to act as a single ring electrode for stimulating and/or sensing during this step. MICC and current fractionalization can be used to provide stimulation at longitudinal locations between the electrodes. As each electrode contact from the proximal to the distal end of the lead is iteratively used as the stimulating electrode, evoked potentials are recorded at one or more of the other electrodes. This iterative process is used to create a comprehensive profile of the sensed evoked potentials relative to the locations upon the electrode lead both along and around the lead. One or more features of the evoked potentials can be extracted from the evoked potentials recorded at each of the sensing/recording electrodes. Generally, any value or metric may be used as the extracted feature(s). Examples of such features of the evoked potentials include but are not limited to:

- a height of any peak (e.g., N1);
- a peak-to-peak height between any two peaks (such as from N1 to P2);
- a ratio of peak heights (e.g., N1/P2);
- a peak width of any peak (e.g., the full-width half-maximum of N1);
- an area or energy under any peak;
- a total area or energy comprising the area or energy under positive peaks with the area or energy under negative peaks subtracted or added;
- a length of any portion of the curve of the evoked potential (e.g., the length of the curve from P1 to N2);
- any time defining the duration of at least a portion of the evoked potential (e.g., the time from P1 to N2);
- latencies of any peaks (P1 . . . Pn, N1 . . . Nn, etc.) as well as other feature-to-feature latencies;
- amplitude decay function;
- a time delay from stimulation to issuance of the evoked potential, which is indicative of the neural conduction speed of the evoked potential, which can be different in different types of neural tissues;
- a conduction speed (i.e., conduction velocity) of the evoked potential, which can be determined by sensing the evoked potential as it moves past different sensing electrodes;
- a rate of variation of any of the previous features, i.e., how such features change over time;
- a power (or energy) determined in a specified frequency band (e.g., delta, alpha, beta, gamma, etc.) determined in a specified time window (for example, a time window that overlaps the neural response, the stimulation artifact, etc.);
- spectral characteristics in the frequency domain (e.g., Fourier transform);
- a cross-correlation or cross-coherence of the evoked potential shape with a target optimal shape; and
- any mathematical combination or function of these features.

Values for the one or more extracted features of the evoked potentials are determined as a function of the longitudinal stimulation locations along the electrode lead. The longitudinal location that yields the optimum value(s) for the one or more features can be selected as the best longitudinal location for providing stimulation. According to some embodiments, the optimum stimulation location may be the stimulation location that provides the maximum value of the evoked potential feature (such as evoked potential amplitude, peak height, etc.), indicating that stimulation at that location best activates targeted neural elements. Alternatively, the optimum stimulation location may be a location that minimizes one or more of the evoke potential features, for example, if that feature is correlated with a side effect. Desired or undesired evoked potentials indicative of an optimum or sub-optimal stimulation configuration (i.e., placement of stimulation and/or stimulation waveform or pulse sequence) may be known a priori, for example, based on the clinician's expectations, literature, historical studies, etc., or correlated in real-time to symptom observations made during the clinical programming session. Targeted evoked potentials may also be "prescribed" on a patient-specific basis, given disease phenotype or targeted brain structures, for example. They also depend on lead placement. It should be noted that the steps for optimizing the best stimulation position on the electrode lead may be performed automatically using one or more optimization algorithms configured to perform the stimulation sweep and to optimize the stimulation location based on the extracted evoked potential parameters. Alternatively (or additionally), the optimization may be performed manually, whereby the clinician manually changes the stimulation locations (using a GUI as described in more detail below, for example) and observes the evoked potentials and extracted features for each stimulation location.

Once the optimum longitudinal stimulation location is determined, the sweeping process may be repeated to optimize the rotational stimulating location by iteratively using different directional electrodes (and/or fractionalized angular locations) to provide stimulation and using the other electrodes as sensing/recording electrodes to record evoked potentials. Again, one or more features may be extracted from the evoked potentials and the rotational position that yields the optimal values for the evoked potential features may be selected as the rotational location for providing directional stimulation. As described above, MICC and current fractionalization may be used to determine optimum stimulation locations that are located between physical locations of actual electrode contacts. Again, the rotational optimization may be performed using optimization algorithms or may be performed manually.

At step 908 impedances at each of the electrode contacts may also be determined. The impedances at each of the contacts may be used to determine an impedance map at the longitudinal and rotational locations along the lead. Impedances may be measured differentially and/or with respect to the can. Other signals may also be measured, for example, local field potentials and/or spontaneous activity.

At step 910, the stimulation locations, i.e., the fractionalizations determined for the longitudinal and rotational stimulation locations, can be saved and stored. Also, the determined evoked potential features, the impedance map, and values for other measured signals, such as local field potentials and/or spontaneous activity can be saved and stored. It should be noted that the workflow 900a may be performed while the patient is under general anesthesia and the measured values may be compared to values obtained by repeating the workflow when the patient is awake.

Figure 9B:
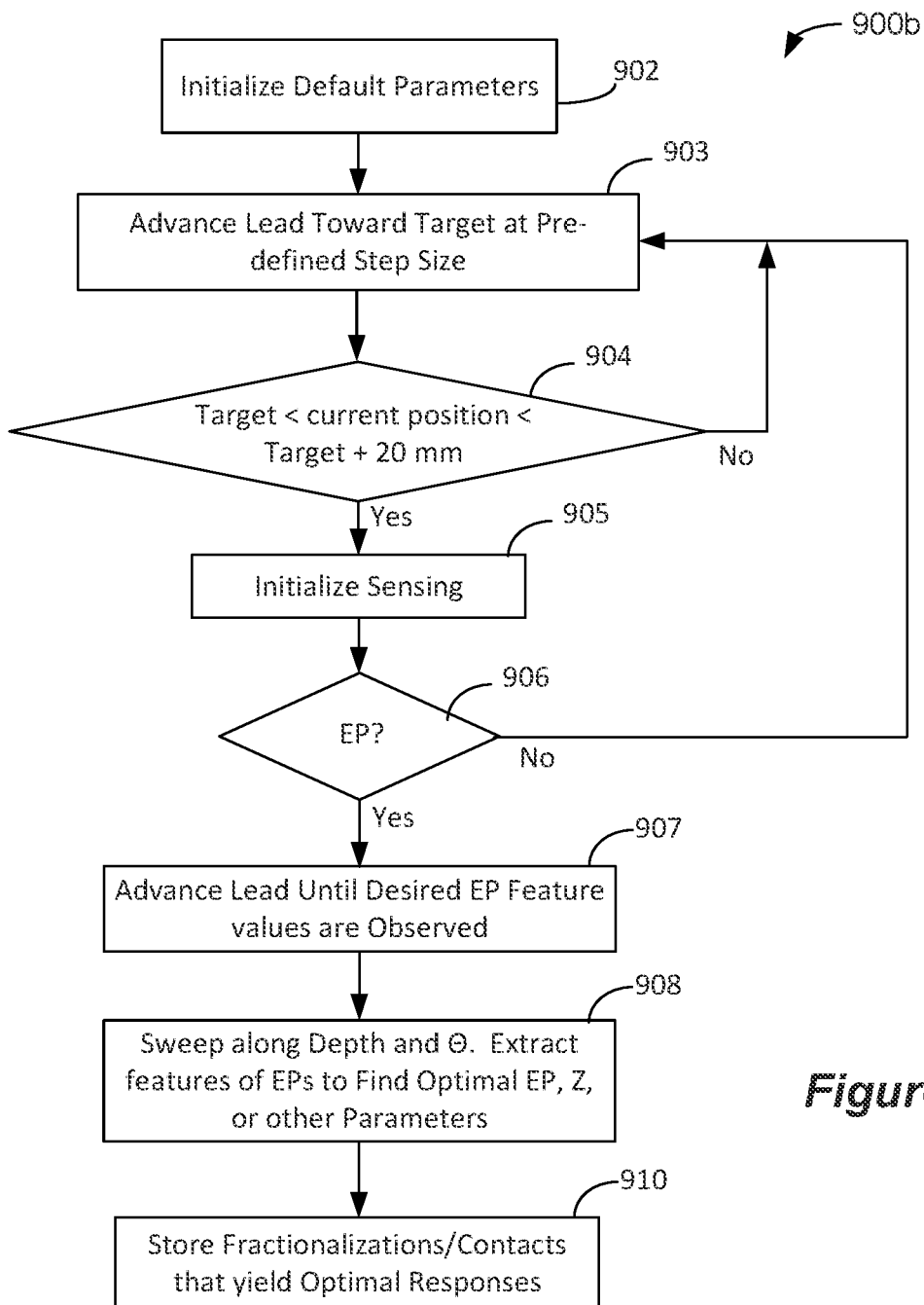
FIG. 9B illustrates a workflow for using evoked potentials to inform implantation of an electrode lead in a patient's brain.

FIG. 9B illustrates a workflow 900b that can be used to facilitate the surgical implantation of an electrode lead at a correct location in a patient's brain. At step 902, an initial set of default parameters is initialized as described above with respect to the workflow 900a (FIG. 9A). At step 903, the lead is advanced toward the target neural elements at a pre-defined step size. The step size may be on the order of 1 mm, for example. The lead may be advanced to within a certain pre-defined distance from the target neural elements. For example, the distance may be 20 mm from the target neural elements (step 904). Once the lead is within the pre-defined distance from the target neural elements sensing, as described above, may be initialized (step 905). Once sensing is initialized, it is determined whether evoked potentials can be detected (step 906). If evoked potentials are not detectable, the lead can be advanced further. Although not illustrated, a parameter sweep, as described above with respect to the workflow 900a (FIG. 9A) may be performed if evoked potentials are not detected. Once evoked potentials are detected, the evoked potentials may be used to guide the lead movement to the optimal lead position (step 907). For example, one or more features may be extracted from the EPs and compared to target values for the feature that are expected when the lead is in the optimum location. For example, the lead may be advanced until a maximum EP amplitude, peak-peak amplitude, or other amplitude is obtained. Once the placement is optimized longitudinal and rotational sweeps may be performed (step 908) as described above (i.e., as per step 908 described with respect to the workflow 900a, FIG. 9A) to determine the optimum location on the lead for providing stimulation based on the extracted features of the evoked potentials. The extracted features of the evoked potentials can also be used to determine whether to advance the lead further with respect to the neural targets to obtain an optimum lead position. As described above, impedances at each of the electrode contacts may also be determined, as well as other signals, for example, local field potentials and/or spontaneous activity. At step 910, the stimulation locations, i.e., the fractionalizations determined for the longitudinal and rotational stimulation locations, can be saved and stored. Also, the determined evoked potential features, the impedance map, and values for other measured signals, such as local field potentials and/or spontaneous activity can be saved and stored.

Figure 10:
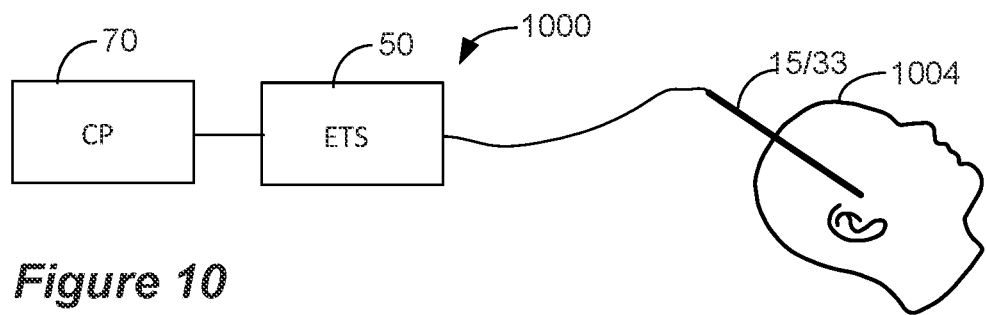
FIG. 10 illustrates a system for implanting an electrode lead in a patient's brain.

FIG. 10 illustrates a schematic of a system 1000 for performing implantation of an electrode lead (e.g., lead 15 or lead 33, FIGS. 1A/1B) in the brain of a patient 1004, as described above (FIG. 9B). The system 1000 also comprises one or more devices for controlling the stimulation and sensing provided at the electrode lead. The illustrated embodiment comprises a clinician programmer (CP) 70 for programming the stimulation and sensing parameters. The functionality of a CP 70 may be like that described above (FIG. 5), for example. The CP used during lead implantation may be the same machine or a different machine as the one used to program the patient's IPG later, during the fitting procedure. The clinician can use the CP 70 to select the electrodes of the lead 15/33 that will be used to provide stimulation, the parameters of the stimulation waveform(s) that will be applied, and the electrode(s) that will be used to sense evoked responses. In the illustrated system 1000, the CP 70 provides those selections to an ETS 50. The ETS 50 causes the stimulation to be applied to at leads. The ETS 50 also receives, and records sensed signals from the lead. The CP and ETS may communicate via a wired or a wireless connection. In the illustrated embodiment, a single ETS component is shown. However, according to some embodiments, multiple components could be used, for example, separate components for providing stimulation and for receiving and recording sensed signals. The CP may communicate with either or both ETS components in such an embodiment. According to some embodiments, aspects of the CP functionality and the ETS functionality may be combined in a single device. For example, the ETS 50 may itself be configured for programming the stimulation and/or sensing parameters. Alternatively, the functionality of receiving and recording the sensed signals (correlated with the stimulation configuration/parameters) may be embodied in the CP 70, for example as a module or subroutine additional to the CP functionality described above. Regardless of the exact configuration, the system is capable of causing stimulation of a defined waveform to be applied using selected one or more electrode on the lead, and of sensing/recording responses evoked by the stimulation. Further, the system 1000 (e.g., in either the CP 70 and/or the ETS 50) comprises control circuitry configured to perform the steps of the various algorithms and methods described with respect to FIG. 9B and those described below. The control circuitry may be so configured by executing program code stored on non-volatile computer-readable media.

Aspects of this disclosure relate to graphical user interphases (GUIs) for acquiring and/or analyzing evoked potentials, for example, while executing workflows, such as the workflows 900a and 900b described above. The GUIs described herein may be provided on one or more external devices used during the surgical implantation of the leads and/or during a fitting process. For example, the GUIs may be provided using a CP 70, as described above (FIG. 5 and/or FIG. 10). The disclosed GUIs allow a user to collect and visualize, identify, and parse signals related to the evoked potentials, analyze those signals in the time domain, frequency domain, and/or other spaces, as may be appropriate. The GUIs also allow a user to save the signals (and/or parameters extracted from the signals) for further uses, such as for closed-loop control of stimulation, tracking the effectiveness of the therapy over time, etc.

Figure 11:
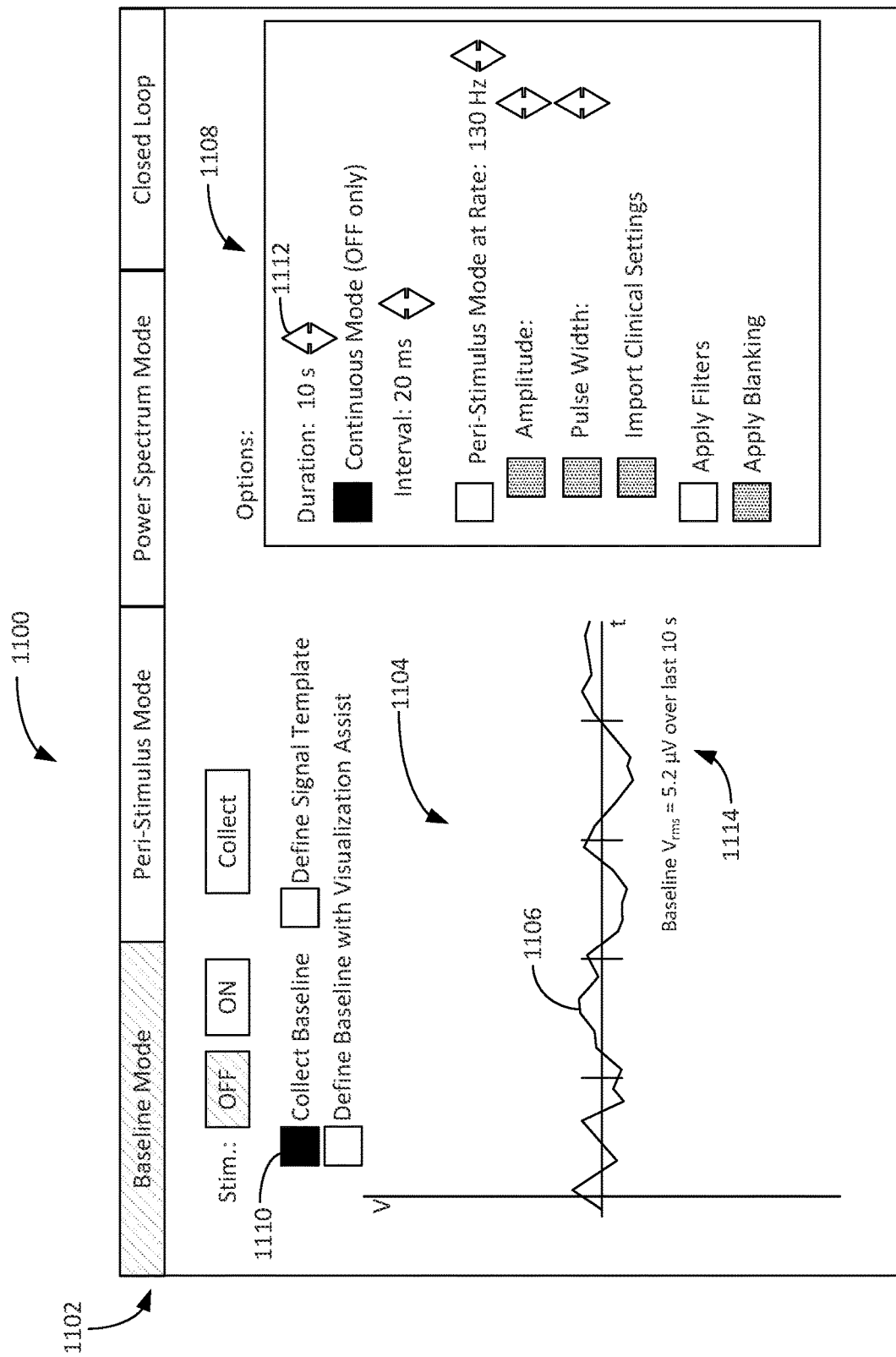
FIG. 11 illustrates an embodiment of a graphical user interface (GUI) for collecting and analyzing evoked potentials.

FIG. 11 illustrates an example of a GUI 1100 for performing aspects of collecting and analyzing evoked potentials, as described herein. It will be appreciated that the GUIs illustrated herein are only examples and that there are many ways of expressing and laying out options for performing the same described functionality. The illustrated GUI 1100 comprises a mode selection bar 1102, whereby various modes may be selected, depending on the task the user wishes to perform. Various of the modes shown in the mode selection bar 1102 will be described below. The GUI 1100 may include a visualization pane 1104 which allows the user to visualize and interact with signals 1106 recorded at the sensing/recorded electrodes and/or traces loaded into the GUI, such as templates and/or saved data, as explained in more detail below. The illustrated GUI may include an options configuration pane 1108, whereby the user may configure parameters and select actions relative to the task the user is performing. Aspects of the GUI may include boxes 1110 and/or arrows 1112 for selecting and adjusting various functions, such as the action to be performed, adjusting stimulation parameters, collection windows/collection parameters, etc. The boxes may be color coded to reflect their selection state (i.e., on/of, active/inactive, etc.) and some boxes may be color coded to indicate that they are not available during a given mode or activity. It will be appreciated that other GUI aspects, such as drop-down or pop-up windows may be used to accomplish the same functionality.

An aspect of sensing and using evoked potentials, as described herein, is that the magnitude of the evoked potentials can be quite small and difficult to distinguish from baseline noise. Thus, embodiments of the disclosed GUIs provide tools to assist the user in elucidating evoked potentials from baseline noise. In the embodiment of the GUI 1100 illustrated in FIG. 11, a baseline mode is selected (as indicated by the fact that "Baseline Mode" is highlighted in the mode selection bar 1102. Note that stimulation is off (as indicated by the highlighting of "Off" next to the stimulation setting). The user has selected to Collect Baseline. Selections in the options configuration pane 1108 show that the baseline is being collected in a continuous mode for a duration of 10 seconds. Thus, the signal 1106 in the visualization pane 1104 represents a 10 second interval of baseline signal sampled with no stimulation. The system can be configured to calculate one or more metrics of the signal, such as the root mean square, interquartile range, or other metrics of signal variability and to display and/or save those metrics. In FIG. 11, the GUI has displayed a running value 1114 of the metric, namely a root mean square of the voltage of the signal over the 10 second interval. Note that during this action, some features, such as the "Amplitude," "Pulse Width," and "Import Clinical Settings" options of the Peri-Stimulus Mode, and the "Apply Blanking" option are locked out (i.e., not available), as indicated by the fact that their corresponding boxes are greyed out.

Figure 12:
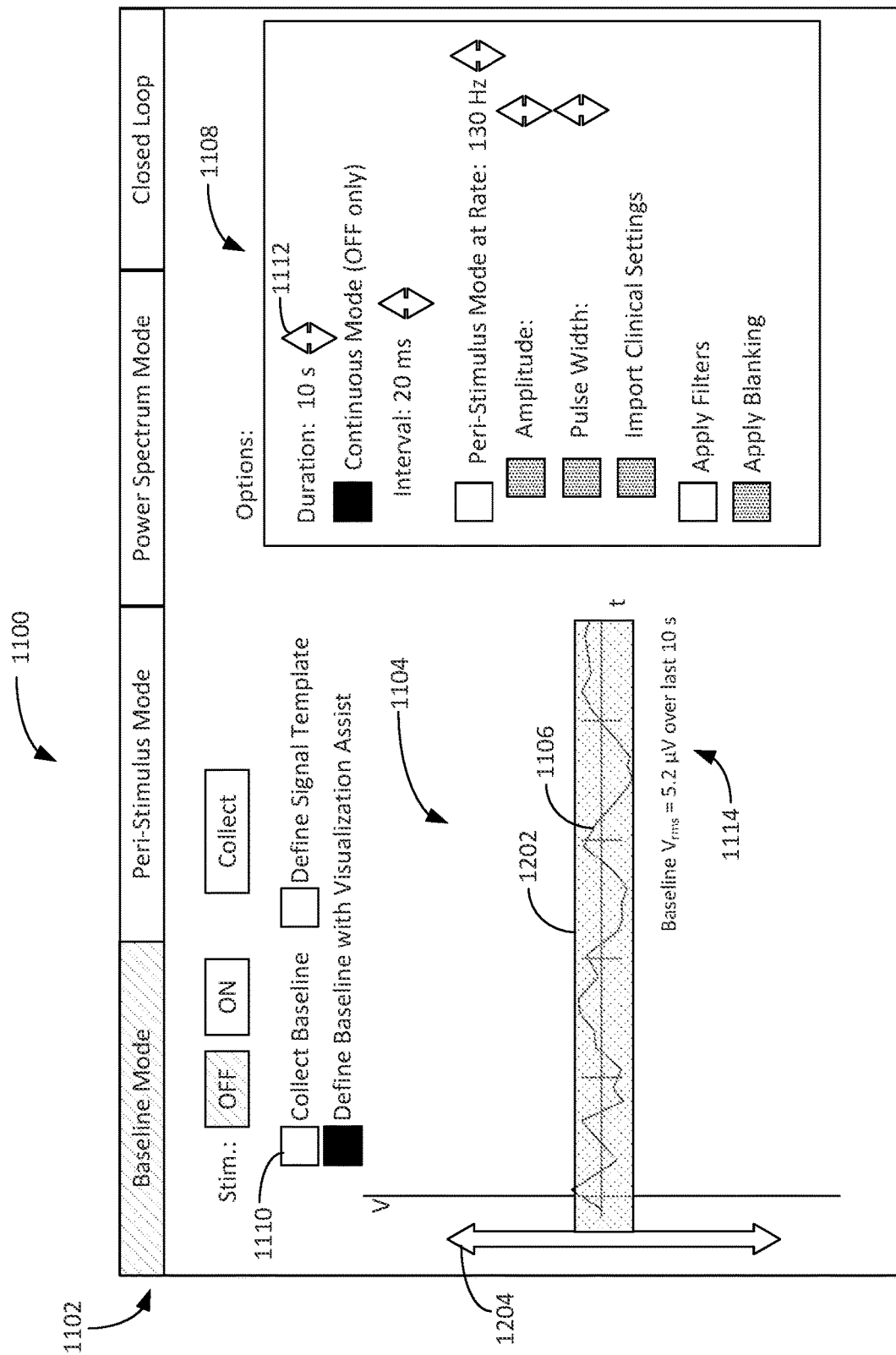
FIG. 12 illustrates an embodiment of a graphical user interface (GUI) for collecting and analyzing evoked potentials.

FIG. 12 illustrates another aspect of the GUI 1100 for helping a user to configure a baseline noise value. Assume that the user has collected and saved a baseline signal 1106, as discussed with reference to FIG. 11. In FIG. 12, the user has selected "Define Baseline with Visualization Assist." The GUI provides a selection box 1202 that the user can use to designate a portion of the signal 1106 that is to be defined as baseline. The user can use the control arrow 1204 to size the selection box 1202 to encompass the portion of the signal that the user wants to save as a baseline. Generally, the user can drag, toggle, click, or otherwise manipulate the selection box 1202. The selected signal is denoted as baseline and is processed as noise in later occurring visualization modes and/or can be set as a threshold for later measurements. The selected baseline can be set a template for subtraction from later measurements.

Figure 13A:
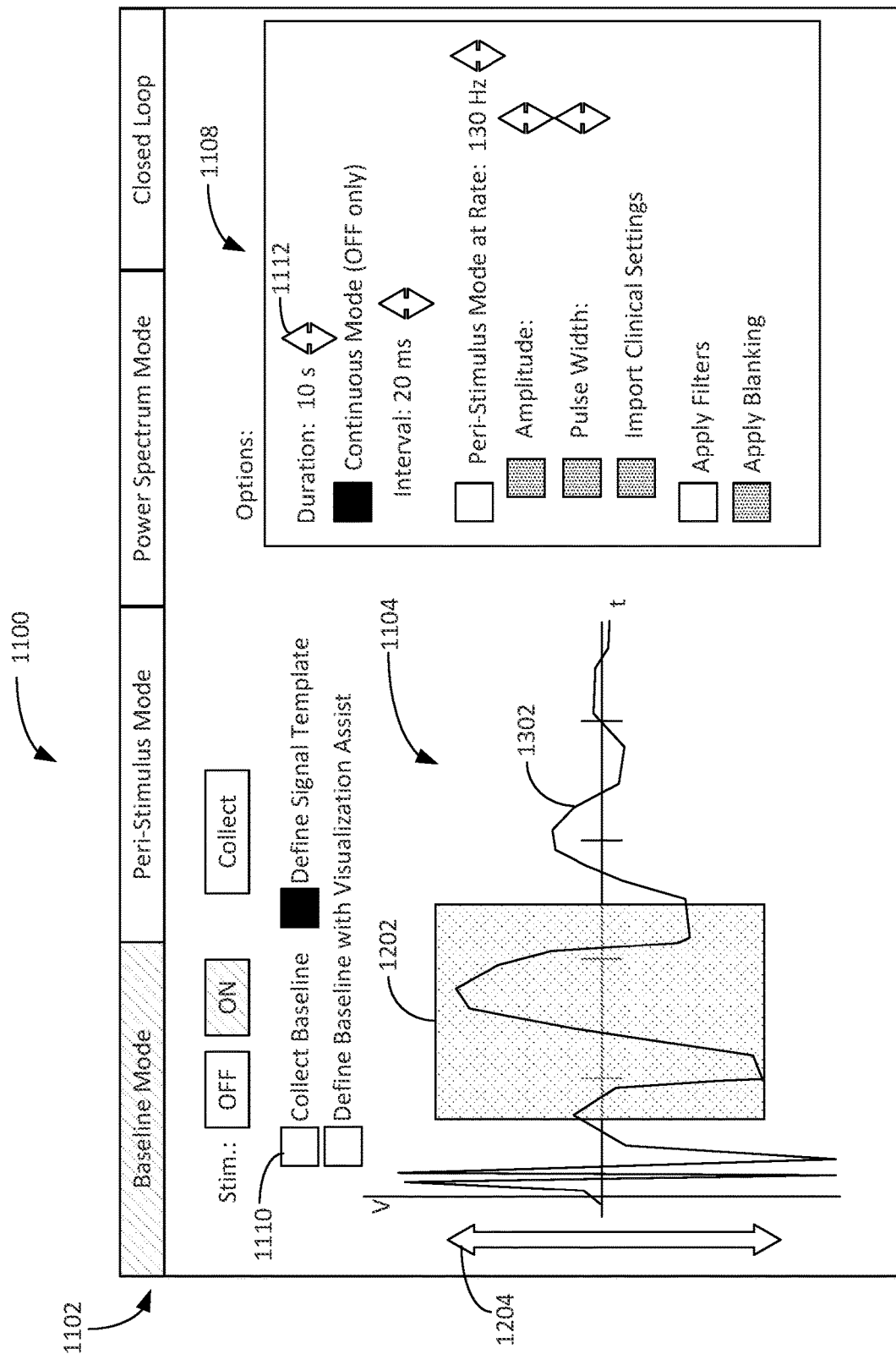
FIGS. 13A and 13B illustrate an embodiment of a graphical user interface (GUI) for collecting and analyzing evoked potentials.
Figure 13B:
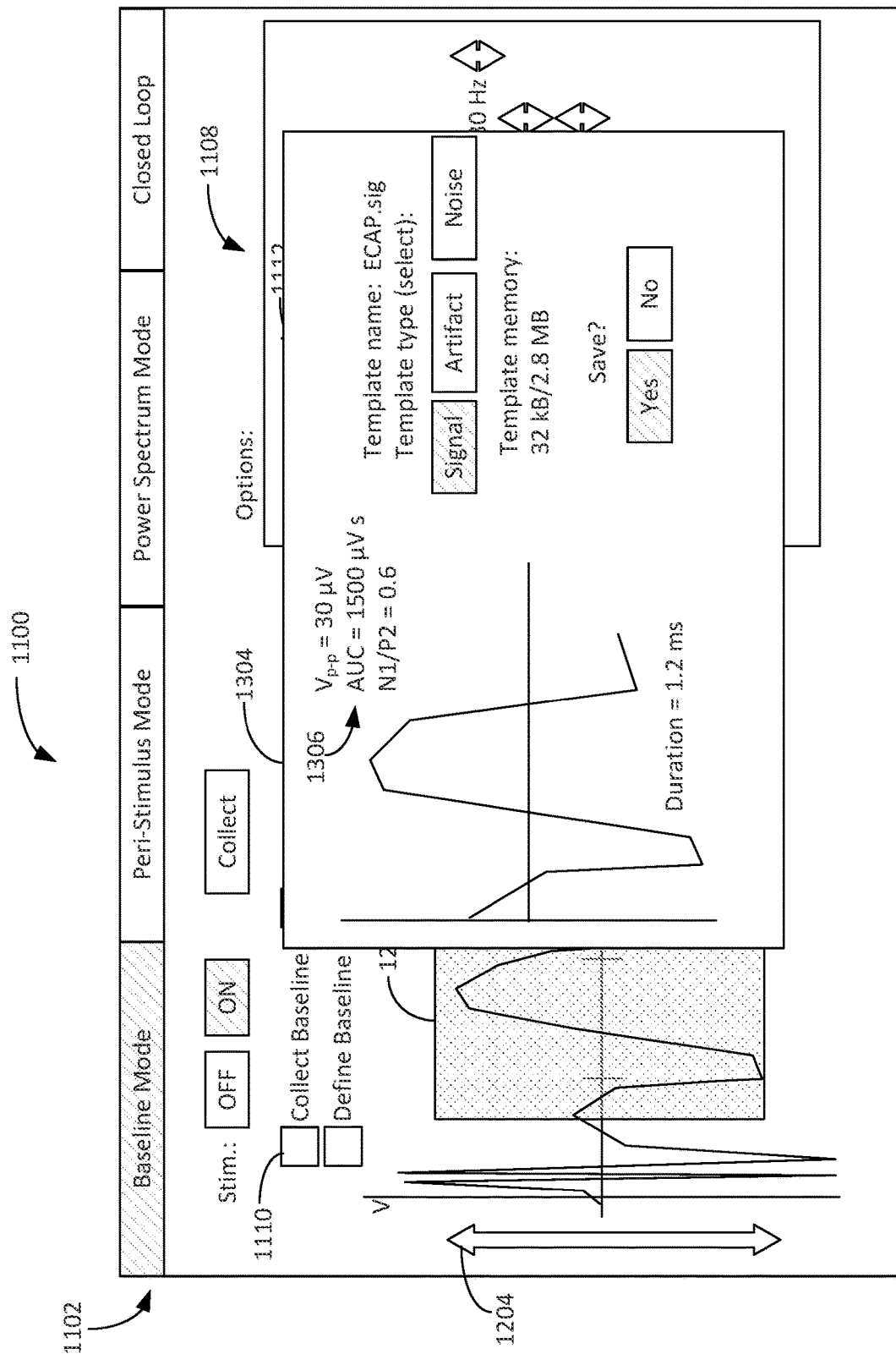

Embodiments of the disclosed GUIs and associated systems allow a user to define and use templates. One example of a template may be the defined baseline signal discussed above, which may be saved and used during later modes, for example, by subtracting the baseline template from another recorded signal. FIGS. 13A and 13B illustrate using the GUI 1100 to capture a portion of a sensed signal and save it as a template. In the GUI illustrated in FIG. 13A, stimulation is now being applied (as apparent because Stim ON is highlighted), and a sensed signal 1302 is displayed in the visualization pane 1104. Assume that the user believes a portion of the displayed signal 1302 contains an evoked response and wishes to tease that evoked response out of the rest of the signal. The user can manipulate the selection box 1202 to encompass the portion of the signal that the user believes contains the evoked response. Again, the user can drag and drop the box and manipulate it using the control arrow 1204, for example. The user can then save the selected portion of the signal as a template. For example, the user can select "Define Signal Template," as shown. Upon selecting to save the portion of the signal as a template, a save template window 1304 may appear, as shown in FIG. 13B. In the illustrated embodiment, the save template window shows the selected portion of the signal and may automatically compute some features 1306 of the save portion of the signal, such as peak to peak amplitude, area under the curve, various peak ratios, and the like. The save template window may allow the user to name the template and specify the type of template, for example, signal, artifact, or noise.

Having saved the extracted portion of the signal as a template, the template can be recalled and loaded into the GUI at a later time. For example, one or more saved templates can be recalled and overlayed on top of subsequently collected signals for comparison purposes. By saving portions of collected signals as templates, the user can accumulate a library of templates containing potentially interesting/informative signal characteristics. According to some embodiments, the GUI may contain a pre-populated library of templates, for example, templates corresponding to various evoked potentials, such as MEPs, ECAPs, ERNA, and the like, and/or other signal line shapes and characteristics to which a user may wish to refer.

Figure 14:
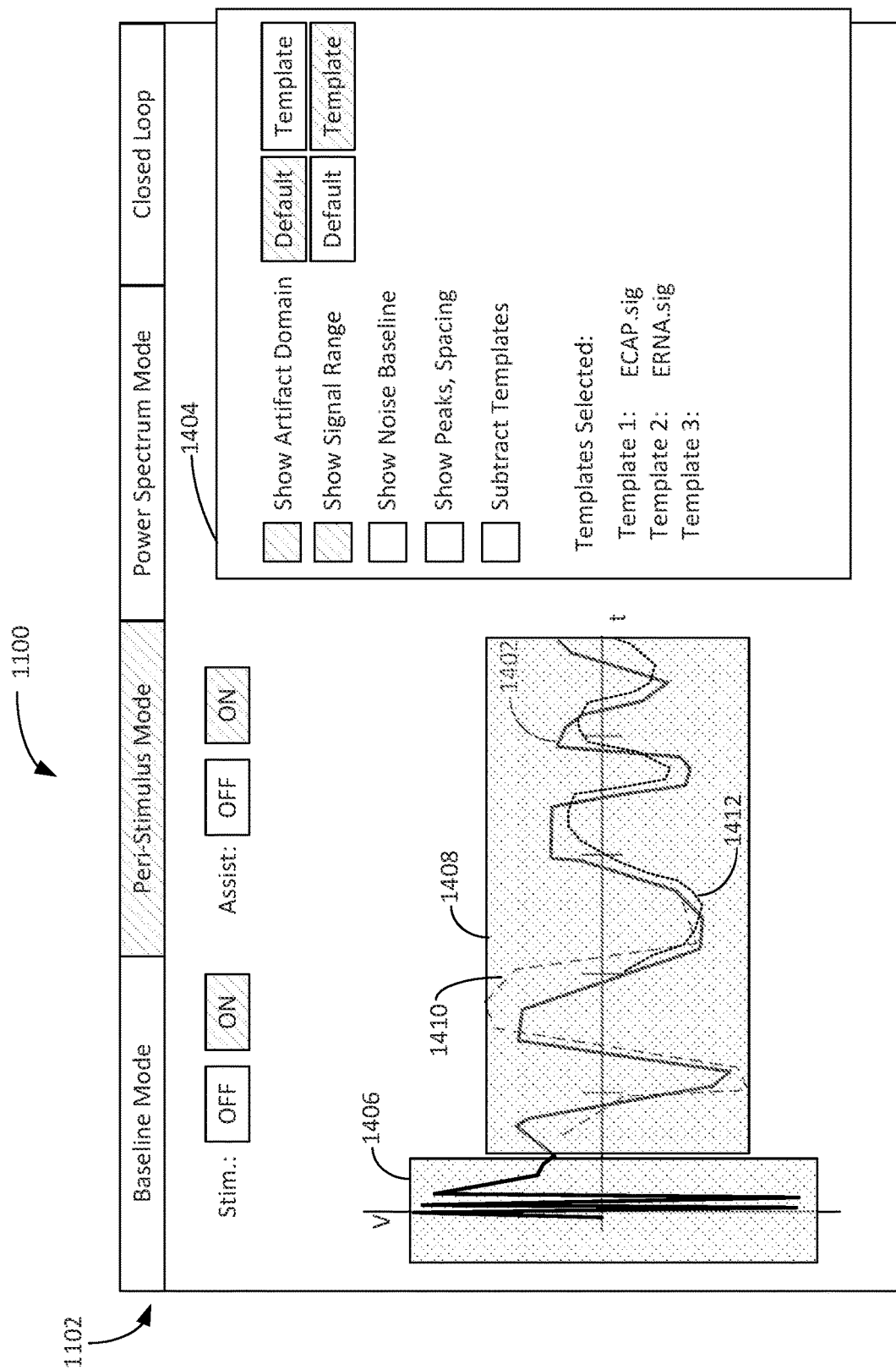
FIG. 14 illustrates an embodiment of a graphical user interface (GUI) for collecting and analyzing evoked potentials.

According to some embodiments, the GUI 1100 may be configured to average sensed signals over multiple stimulation epochs. This is illustrated in FIG. 14 and referred to in the illustrated GUI as a Peri-Stimulus Mode. The bold signal 1402 represents an average of signals collected over several stimulation epochs and time-aligned with respect to the stimulation pulse. The alignment may be accomplished using internal clocking based on the stimulation pulse or may be based on characteristic features of the signal, for example, by aligning the stimulation artifact.

The GUI 1100 may be configured with assist functions to aid the user as they interact with the recorded signals. The assist function may help the user identify various features of the recorded signals, either based on templates from the template library and/or based on intelligence that is programmed into the GUI. For example, the GUI may be pre-programmed with information relating to the time domain in which stimulation artifacts typically occur. Likewise, the GUI may be pre-programmed with line shapes and other attributes of various evoked and spontaneous potentials, such as ERNA signals, ECAP signals, and the like. A sophisticated user may supplement or modify such programming, according to some embodiments.

Notice that in FIG. 14, Assist is selected. Accordingly, an assist window 1404 is displayed, which includes a menu of various assist functions available in the present mode. In the illustrated configuration, the user has chosen to display a box denoting the domain of the signal corresponding to stimulation artifact 1406, which is based on default intelligence programmed into the GUI. The user has also chosen to display a box denoting the signal domain 1408, which in this case is based on a template. Other available assist functions in the illustrated example, include the ability to show the noise baseline (for example, the baseline collected earlier), automatically identify peaks and/or peak spacing in the signal, and to subtract templates (such as a stimulation artifact template) from the displayed signal. In the illustrated example, the user has also loaded and overlayed two templates onto the averaged sensed signal. Specifically, the user has overlayed an ECAP template 1410, which may be the ECAP.sig template save earlier (FIG. 13B), and an ERNA.sig template 1412, which may have been previously saved or that is otherwise available in the template library. The user may use such overlayed templates as visual aids in evaluating the displayed average signal.

Figure 15:
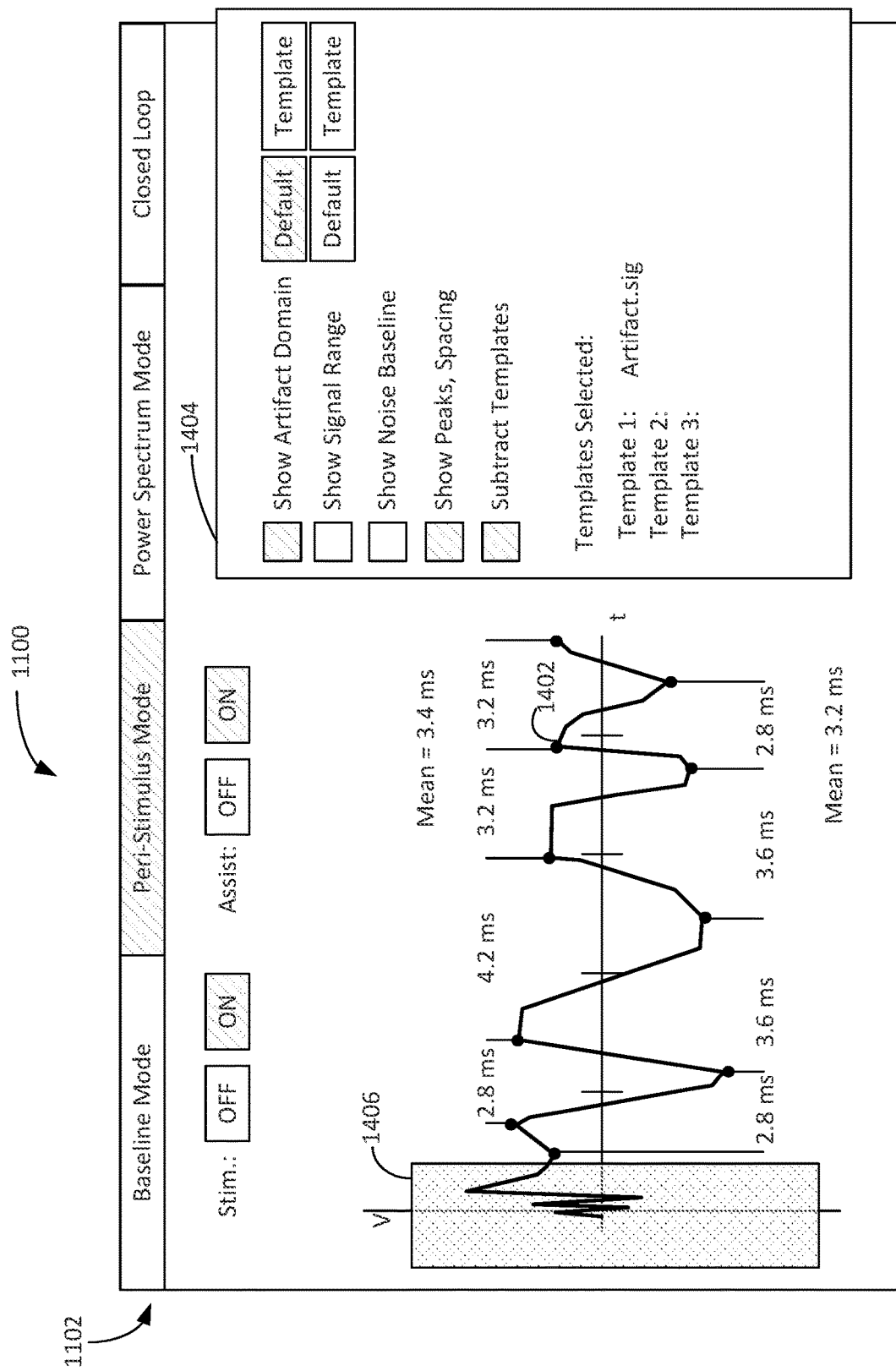
FIG. 15 illustrates an embodiment of a graphical user interface (GUI) for collecting and analyzing evoked potentials.

FIG. 15 shows another examples of using the GUI's assist functions 1404 to analyze aspects of the averaged sensed signal 1402. In this illustrated embodiment, the user has selected to load a template of a stimulation artifact ("artifact.sig") and subtract that template from the measured signal 1402. Notice that the stimulation artifact is significantly reduced compared to FIG. 14. The user has also instantiated a feature that identifies the maxima and minima of the signals ("Show Peaks, Spacing") and shows the spacing between the maxima and between the minima. Such labeling can help the user identify evoked potentials, such as ERNA.

Figure 16:
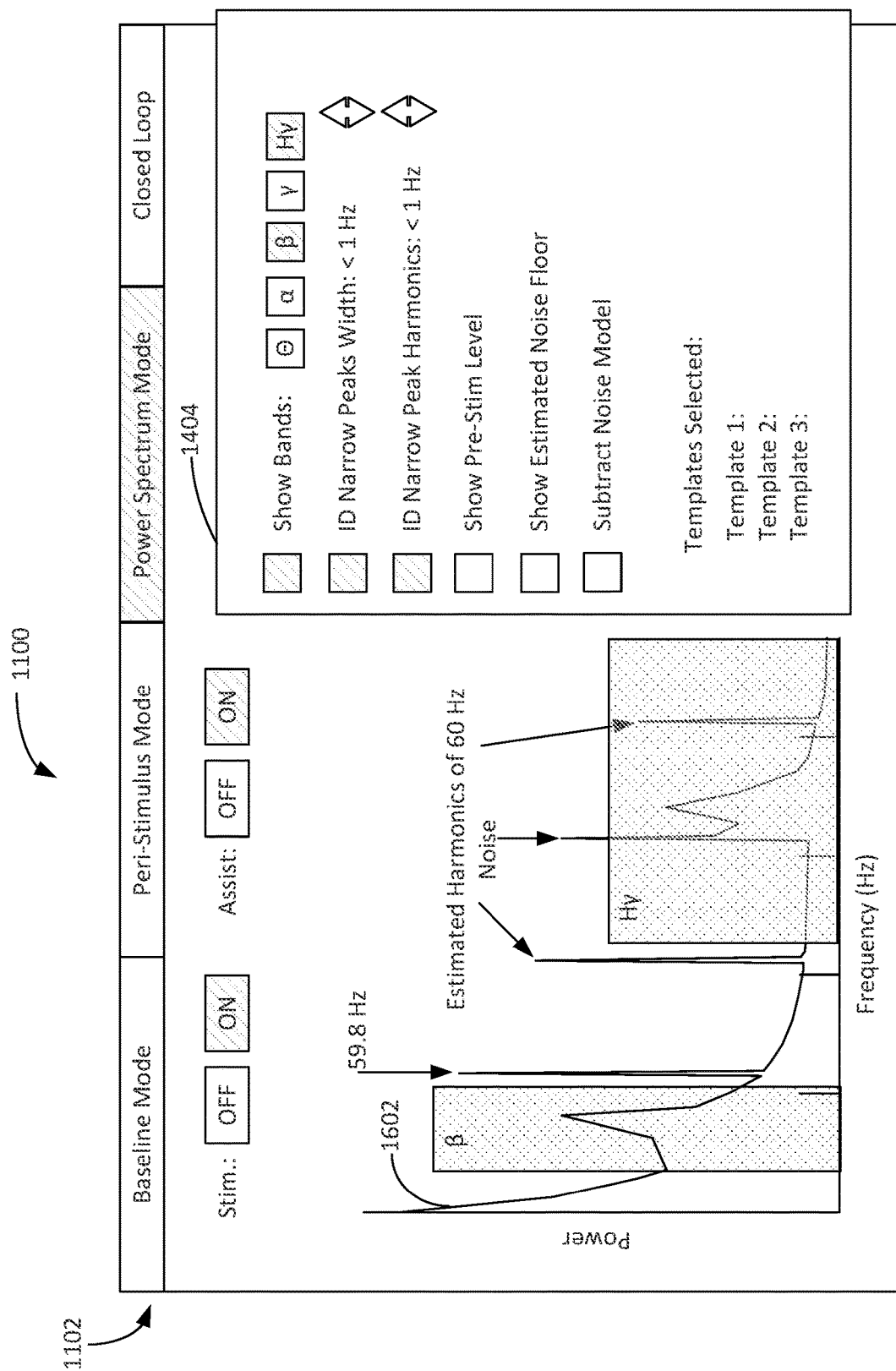
FIG. 16 illustrates an embodiment of a graphical user interface (GUI) for collecting and analyzing evoked potentials.

Embodiments of the GUI 1100 can be configured to display and analyze sensed signals in the frequency domain, as illustrated in FIG. 16. Notice that Power Spectrum Mode has been selected and the visualization pane 1104 presents a spectrogram signal 1602 as power as a function of frequency. The spectrogram may be computed using a Fourier transform (FT), fast Fourier transform (FFT) or other representations of the frequency space. The assist window 1404 now presents various assist functions that are useful for analyzing the spectrogram signal. For example, the GUI can be configured to identify noise with a known frequency distribution, such as 1/f noise. The GUI can be configured with assist functions to analyze the location and shape of peaks in the spectrogram. According to some embodiments, the GUI can be configured to show expected frequency ranges for known brain oscillations, such as theta, alpha, beta, gamma, and high gamma bands. The user can toggle the display of such bands. In the illustrated instantiation, the user has selected to show expected ranges for the beta and high gamma bands. The bands may be configurable by the user and can be relevant to the patient's disease state. The GUI may be configured to recognize peaks that are likely due to noise, for example, peaks that are excessively narrow. In the illustrated embodiment, the user has selected to mark peaks with widths less than 1 Hz. The peak width may be adjusted, for example, using the illustrated arrows. Notice that the illustrated spectrogram contains a narrow peak at about 60 Hz, which is likely due to electromagnetic interference. The GUI can also be configured to recognize harmonics of suspected interference signals, as illustrated. According to some embodiments, the GUI can be configured to automatically blank such interference signals from the spectrogram. As in the other modes described above, the GUI can be configured to save portions of the spectrogram as templates and/or load and overlay saved template files on top of the spectrogram.

Figure 17:
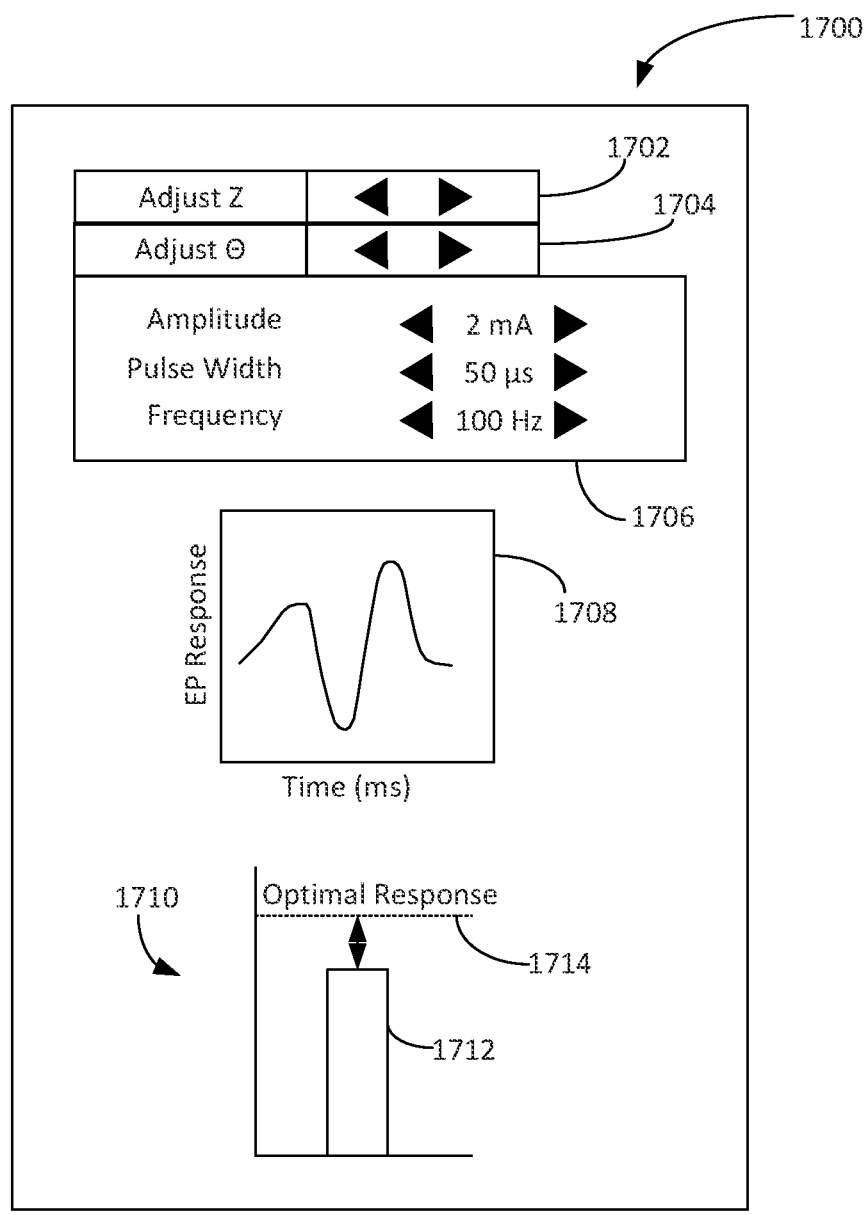
FIG. 17 illustrates an embodiment of a GUI configured for adjusting the stimulation location on an electrode lead.

FIG. 17 illustrates another embodiment of a GUI 1700 that is configured for adjusting the stimulation location on an electrode lead. The GUI 1700 includes control elements for adjusting the longitudinal location 1702 and the angular location 1704 of the center point of stimulation. Inputs to the control elements 1702 and 1704 are transmitted to the stimulation circuitry of the IPG 10 (or ETS 50) to control the fractionalization of current to the electrodes. As described above, current fractionalization/MICC can be used to configure stimulation locations that are between physical electrode locations on the lead. The GUI 1700 also includes control elements 1706 for adjusting stimulation parameters, such as amplitude, pulse width, and frequency of the stimulation waveforms. The GUI 1700 also includes a visualization pane 1708 that can display a representation of evoked potentials (or other signals) present at the sensing/recording electrodes. The GUI 1700 may also include an optimization pane 1710, that provides a visual aid to the user for optimizing the stimulation based on one or more features of the evoked potentials. In the illustrated embodiment, the optimization pane 1710 displays an indicator bar 1712 indicative of a value of one or more of the extracted evoked potential features (e.g., height of a selected peak, area under the curve, etc.). As the user adjusts the longitudinal and/or angular location of the center point of stimulation and/or adjusts the stimulation parameters, the indicator bar 1712 changes to provide a visual indication of changes in the value of the evoked potential feature. The user can use the indicator bar to maximize the value of the feature. According to some embodiments, the optimization pane 1710 may include an indication of an optimum response 1714 for the evoked potential feature. The optimum response value may be based on expected responses gleaned from literature, group clinical data, etc. The user can try to obtain a stimulation location and stimulation parameters that result in the optimum response.

As has been explained, the methods and systems described above use sensed/recorded electrical signals during the surgical implantation of the electrode lead(s) into the patient's brain to optimize the placement of the lead(s) with respect to the targeted neural tissue. The methods and systems can also use the sensed/recorded electrical signals post-operatively to optimize the location upon the lead for providing stimulation and also for optimizing the stimulation parameters. For example, the methods and systems allow a user to record and visualize electrical phenomena occurring in the patient's tissue at the various electrode contacts. Electrical measurements can include measuring evoked potentials, such as MEPs, ECAP, ERNA, etc., as well as spontaneous activity, such as local field potentials. Various features can be extracted from these signals, as described above, and used to guide the placement of the lead and/or to optimize the stimulation location and stimulation parameters. The electrical measurements also include measuring the impedance at the electrode contacts. A further aspect of the disclosure involves saving the results of the various electrical measurements, such as the contact impedances, the evoked response features, etc., and tracking the values over time as the patient undergoes chronic stimulation therapy to inform programming decisions and troubleshooting declines in efficacy that may occur.

Figure 18:
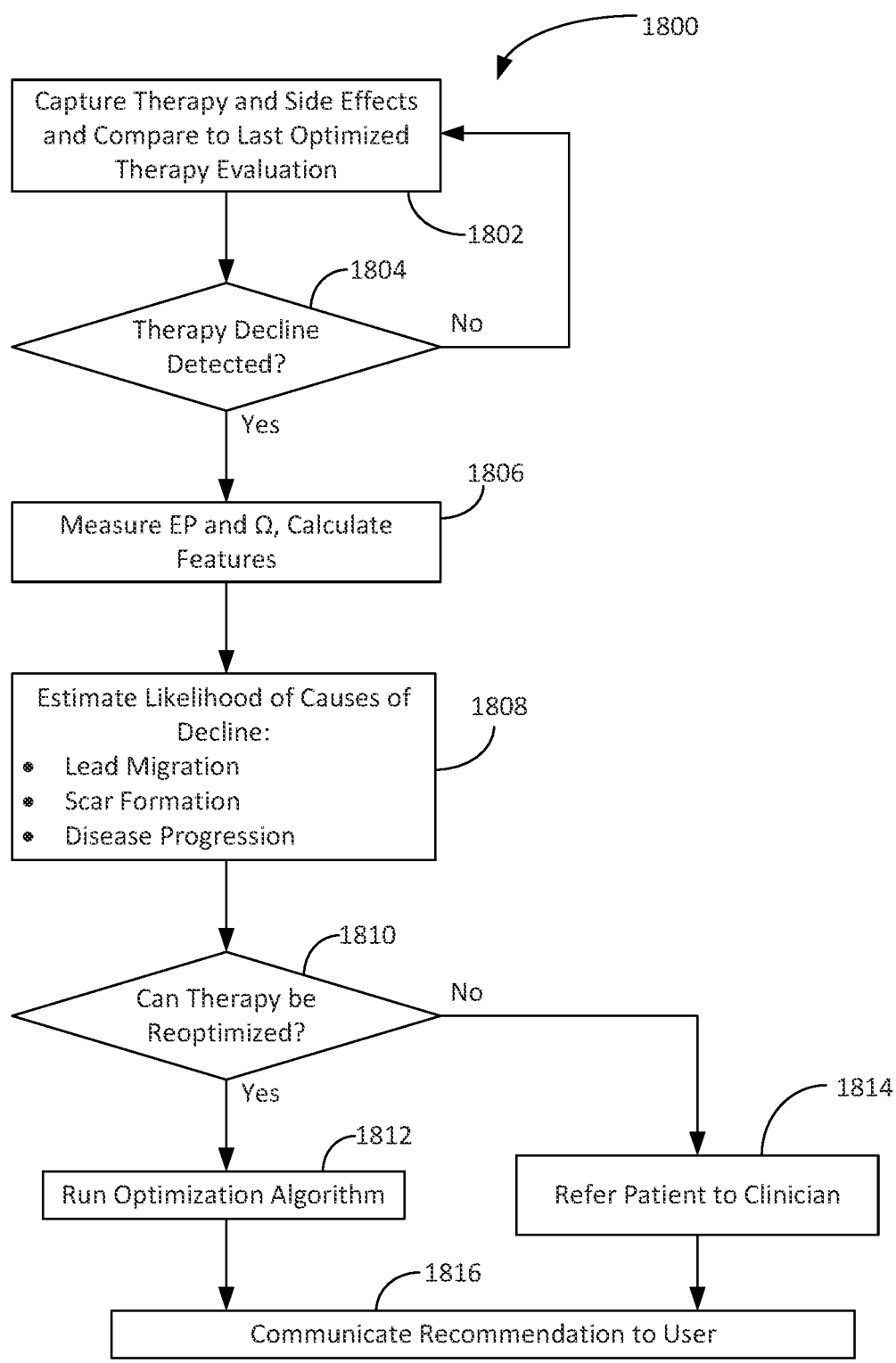
FIG. 18 illustrates a workflow for assessing a decline in therapeutic efficacy of stimulation therapy.

FIG. 18 illustrates an embodiment of a therapy tracking workflow 1800 for using evoked potential features, impedance measurements, etc., to diagnose potential declines in efficacy. The algorithm herein may be broadly described a machine learning algorithm that can capture the feature-set (i.e., the previously described evoked potential features and impedances), analyze them and classify them into various states of therapy decline, such as lead migration, scar tissue formation and disease progression. Assume that a patient has been implanted with a lead and stimulator device (e.g., and IPG). Also assume that the stimulator device is programmed with baseline values for the one or more features of the evoked responses, impedances, and other electrical measurements described above. For example, such measurements may have been acquired and saved during the surgical lead implantation and/or fitting of the stimulator, as described above. At step 1802, the system captures an indication of the therapy and side effects and compares the values to the last optimized therapy evaluation and at step 1804 determines if a decline in therapy is detected. Steps 1802 and 1804 may be executed by one or more algorithms in the IPG, which periodically determines values for the evoked potential features and impedances and compares the determined values with the stored baseline values. A marked deviation of the measured values from the stored baseline values may be indicative of a decline in therapy. The algorithm may also track the values of the features derived from evoked potential spontaneous neural activity and impedances to identify trends for the values over time. Such algorithms may be embodied in the sensing/feedback algorithms 140 (FIG. 6) of the IPG, for example. Alternatively (or additionally) a decline in therapy may be determined based on patient therapy ratings that the patient inputs into their external controller 60 (FIG. 5) or another connected computing device.

At step 1806, if a decline in therapy is detected, algorithms in the IPG measure the impedances at each of the electrode contacts and measure the evoked potentials evoked using the present stimulation settings. The algorithms determine the relevant features of the evoked potentials, as described above, such as peak amplitudes, area under the curve, latency, etc. At step 1808, the algorithm compares the measured values to the pre-recorded baseline values (or multiple values of the features tracked over time) to estimate likelihoods for various problems that could be responsible for the decline in therapy. Further details about how such likelihoods are determined are discussed below, with reference to FIG. 19. At step 1810, the algorithm determines whether therapy might be recovered by adjusting stimulation parameters. This determination may be made based on the type of fault detected at step 1808 and/or the extent of the deviation of the measured features compared to the baseline values. The algorithm may be programmed with evaluation criteria for making such a determination. For example, extensive scar tissue formation at critical electrode leads might invalidate those electrode leads for use, rendering the chances of recovering therapy very low. As another example, electrode migration, if not too drastic, might be recoverable by using different electrodes for providing stimulation. If the algorithm determines to attempt to recover optimum therapy, at step 1812 the algorithm instantiates a sequence, similar to the workflow 900 (FIG. 9A), whereby the algorithm sweeps stimulation parameters and locations at various longitudinal and angular positions on the electrode lead while recording evoked potentials at the non-stimulating electrodes. Using features extracted from the recorded evoked potentials, the algorithm attempt to find the optimum longitudinal and angular stimulation location, as described above. Thus, the algorithm can attempt to remap the electrodes to provide the best stimulation location on the lead, for example, using MICC and current fractionalization, as described above, to recover the best therapy. If at step 1810 the algorithm determines not to try to recover the optimum therapy, the patient may simply be referred to the clinician (step 1814). In either case, information relating to the decline in therapy and a recommendation to see the clinician may be communicated to the patient, for example, via a message sent the patients external controller, smart phone, or other connected computing device (step 1816).

Figure 19:
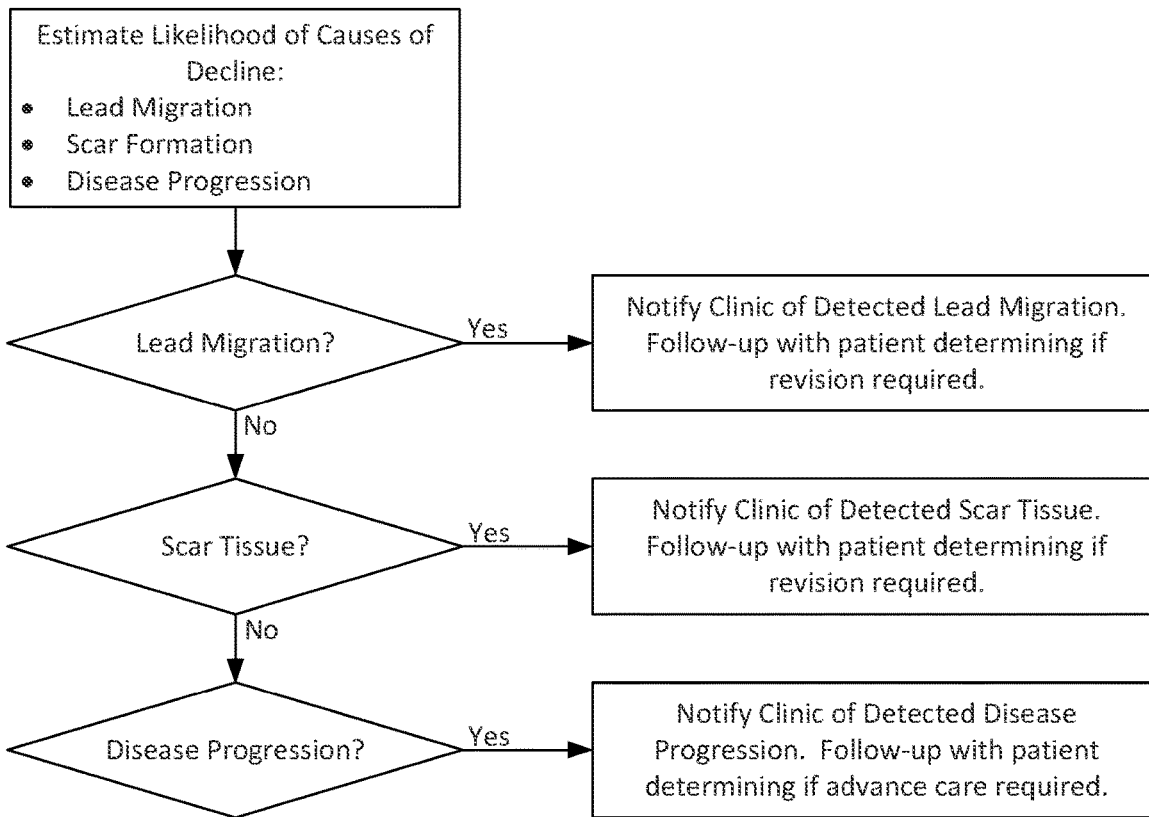
FIG. 19 illustrates a workflow for determining a cause for decline in therapeutic efficacy of stimulation therapy.

FIG. 19 illustrates actions that the therapy tracking algorithm may take depending on various problems that are determined to have caused a decline in therapeutic efficacy. It should be noted that each of the various causes, i.e., (1) lead migration, (2) scar tissue formation, and (3) disease progression are presented in FIG. 19 as binary branching points. However, according to some embodiments, the therapy tracking algorithm may be configured to associate probabilities to each of the causes and proceed accordingly. For example, the algorithm may determine that a particular decline in therapeutic efficacy is 60% likely to be due to lead migration, 30% likely to be due to scar tissue formation, and 10% likely to be due to disease progression. According to some embodiments, the therapy tracking algorithm is programmed with various indicators for each of the potential problems shown in FIG. 19. The indicators may be based on the behavior of the evoked potential features and the impedance measurements over time, as well as other factors, such as the time course of the decline in efficacy. The algorithm may assign weights to each of these indicators to derive probabilities for the factors responsible for the decline in efficacy. For example, an indicator for lead migration is the abruptness of the onset of the decline in efficacy. The efficacy may decline very abruptly or may decline over a period of weeks or months after surgery. The onset is typically different for disease progression, which typically will cause the efficacy to decline over months or years. Another indication of lead migration is that when the algorithm attempts to reoptimize therapy (step 1812, FIG. 18), for example, using the protocols described for workflow 900 (FIG. 9A), it is found that the optimum center point of stimulation has changed positions on the lead. This can indicate that the lead has shifted longitudinally or rotationally with respect to the target neural tissue. The impedance is a good indicator for scar tissue formation, which typically causes the impedance at one or more of the electrodes to increase.

As shown in FIG. 19, once the therapy tracking algorithm has determined a likely cause for a decline in efficacy, the clinician may be notified as such. For example, the IPG may be configured to communicate with an application installed on a patient's smartphone or other internet-connected device, which is configured to relay the findings to a clinician and/or device manufacturer representative. The connected device can also be configured to relay a message to the patient, encouraging them to make an appointment with their clinician.

The previous embodiments involve determining lead migration, i.e., lead movement, as a possible cause of a decline in efficacy during ongoing, chronic therapy. But inadvertent lead movement can also occur prior to ongoing chronic therapy. For example, the lead may inadvertently move during, lead implantation. Such inadvertent lead movement can impact the operation of algorithms, such as the algorithm 900*b* (FIG. 9B) that use features extracted from EPs to help direct lead implantation. Likewise, the lead may move after the lead is implanted and before or during stimulation location optimization (i.e., sweet spot determination) using an algorithm like 900*a* (FIG. 9A). If stimulation location parameters (e.g., pole configurations) determined during the lead implantation are used as default/initial parameters for the sweet spot algorithm, those default parameters may be unreliable if the lead has moved during the interim. Accordingly, the inventors have developed algorithms to check for inadvertent lead movement within the context of performing other algorithms, such as algorithms to assist in lead implantation and/or optimizing stimulation location upon an electrode lead. The algorithms may also be configured to confirm that expected/intentional lead movements have occurred. It should be noted here that lead movement may be longitudinal movement and/or it may be rotational movement or it may be more complex. As mentioned above, longitudinal movement refers to movement parallel with the long axis of the lead (e.g., axis 31, FIG. 1B). Rotational movement refer to rotation about that axis.

Figure 20:
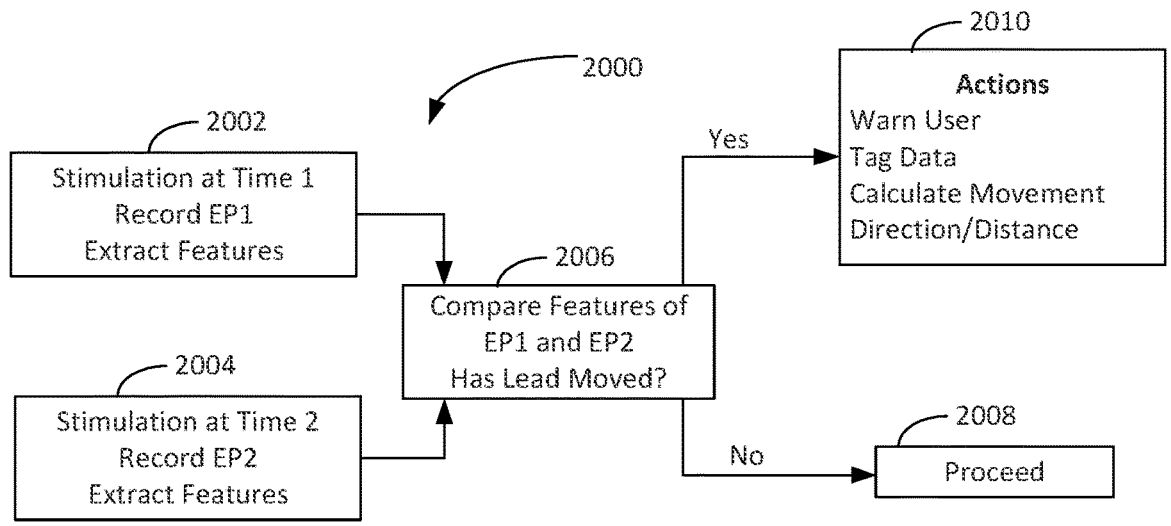
FIG. 20 illustrates a lead movement detection algorithm.

FIG. 20 illustrates an embodiment of a lead movement detection algorithm 2000. The algorithm 2000 is configured to determine if an electrode lead has moved between a first time (Time 1) and a second time (Time 2). The first and second times may be different moments during the performance of another lead optimization algorithm, such as during lead implantation (e.g., algorithm 900*b*, FIG. 9B), during stimulation parameter optimization (e.g., sweet spot searching, as in algorithm 900*a*, FIG. 9A), or the like. The first and second times could also be an interim between a first algorithm and a second algorithm. For example, Time 1 may be at the conclusion of the lead placement operation and Time 2 may be at the beginning of stimulation optimization (which may be days or weeks later). The algorithm 2000 may be executed using whatever computing system is used for the lead optimization algorithm(s). For example, in the context of lead implantation, the algorithm 2000 may be executed using a system 1000 (FIG. 10), which, as described above, is configured to assist lead implantation. For example, the movement detection algorithm 2006 may be executed using the CP 70 in the operating room. Likewise, if the other lead optimization algorithm is stimulation parameter optimization (e.g., stimulation location optimization), the algorithm may be executed on the CP 70 in the clinician's office.

Evoked potentials EP1 and EP2 are recorded at times 1 and 2 respectively (steps 2002 and 2004). Features are extracted from the recorded potentials, as described above. The EP features may be any of the features described above. At step 2006 the algorithm 2000 compares the extracted features to determine if the lead has moved. The comparing step may comprise determining a difference between the EP1 and EP2 features and determining if the similarity meets one or more criteria, or similarly if the difference exceeds a predetermined threshold. If the difference does not exceed the predetermined threshold the algorithm may determine that lead movement has not occurred, and the user may proceed with whatever lead optimization algorithm is in process (step 2008). If the difference does exceed the threshold, then the algorithm may take one or more actions (step 2010). One action is that the algorithm may warn the user, via a user interface of the CP 70, that the lead has moved. The algorithm may associate a tag with any data determined during the underlying lead optimization algorithm, so that if such data is used during further downstream processes that data is marked to indicate that the lead has moved since the data was acquired.

Figure 21:
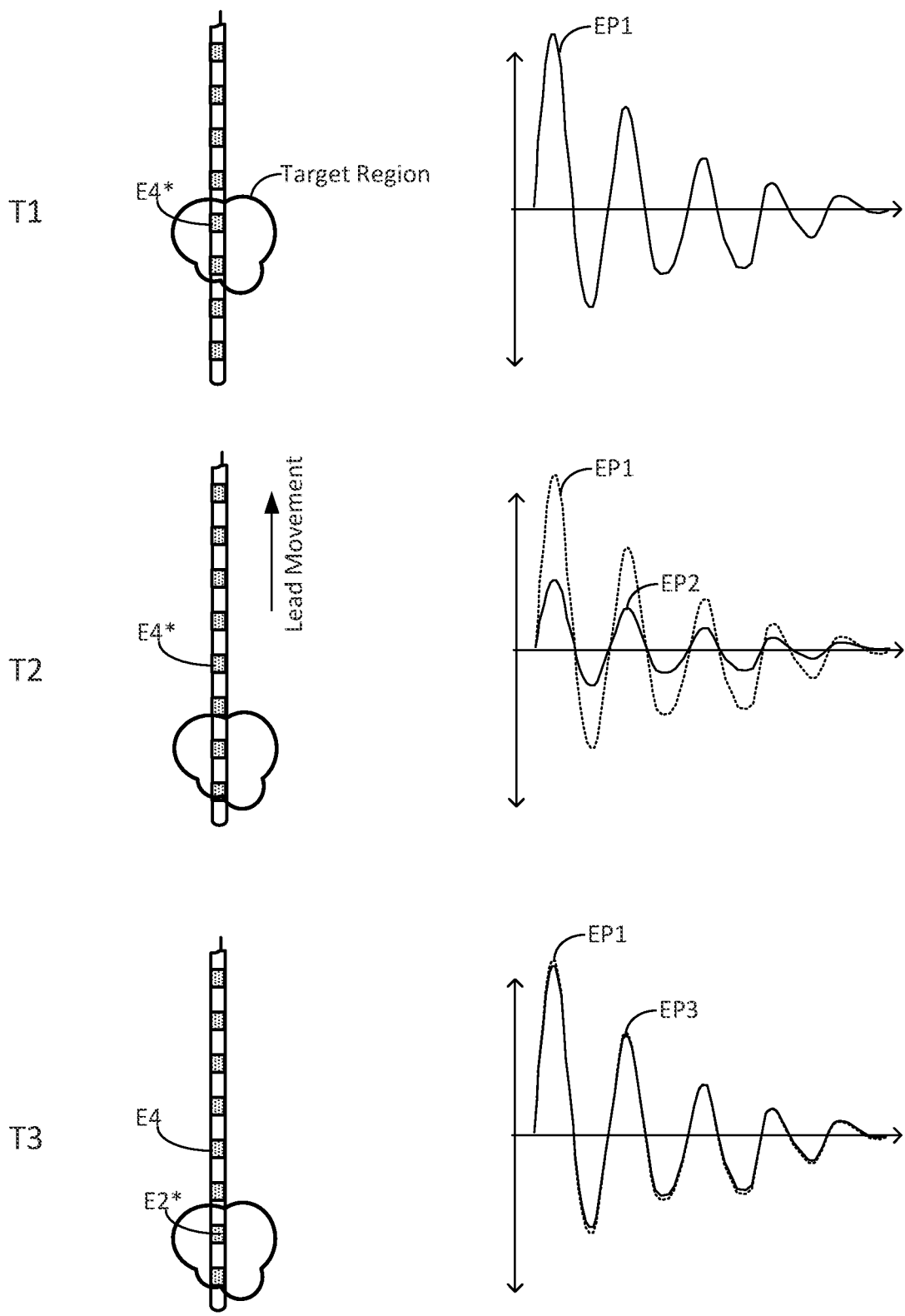
FIG. 21 illustrates a method of determining a distance a lead has moved.

According to some embodiments, the lead movement algorithm 2000 may be configured to determine the nature of any inadvertent lead movement. For example, the lead movement algorithm 2000 may determine if the lead has moved longitudinally (i.e., parallel to the long axis of the lead) and/or if the lead has rotated. According to some embodiments the algorithm may be configured to determine a distance that the lead has moved. If lead movement is more complex, the algorithm may determine a movement vector (direction and magnitude). FIG. 21 shows one embodiment of how a longitudinal distance of lead movement may be calculated. Initially (at time T1), assume that the electrode lead is positioned such that the electrode E4 is located within a target region. When the electrode E4 is used as the stimulating electrode (denoted by the asterisk), an evoked potential EP1 is measured at a recording electrode. At a second time (T2) the lead has moved, as indicated in the drawing, such that the stimulating electrode E4 is no longer located within the target region. Stimulation at E4 evokes an evoked potential EP2, which is weaker than the initial evoked potential EP1. The lead movement algorithm 2006 may note the lead movement based on the difference between the features extracted from EP2 compared to the features extracted from EP1. The lead movement algorithm may perform a longitudinal sweep of the electrode contacts at each longitudinal position whereby each electrode can iteratively be used as the stimulating electrode in an attempt to recover a recorded evoked potential having the same or similar amplitude as the evoked potential EP1. According to some embodiments, the sweep may include positions between electrodes (i.e., "virtual electrodes"). In the drawing, at time T3 it is determined that stimulation at the electrode E2 results in an evoked potential E3 that is substantially similar to the original evoked potential EP1. It can be surmised that the electrode E2 is in the same location previously occupied by electrode E4 based on that observation. Since the spacing between the electrodes is known, the longitudinal distance the electrode has moved can be calculated. Appreciate that the same methodology described here for longitudinal movement can also be used to determine an extent to which lead rotation has occurred. In other words, a degree of rotational movement can be calculated by sweeping the directional leads to determine a new rotational stimulation position that results in the previous EP features. According to some embodiments, the algorithm may determine ratios of amplitudes relative to each other, rather than absolute values of amplitudes. In the above example, for instance, the ratio of the EP amplitude resulting from stimulation at E4 at time T1 relative to stimulation at other electrodes may be higher, indicating that the electrode E4 is located in the target region. If lead movement is detected, the algorithm may seek to determine a new stimulation location that recovers the same or similar ratios of EP amplitudes as observed previously. Different methods of evoking, recording, and comparison may be used to the same effect. It may still be possible to determine whether a move has occurred even when the information that may be obtained from evoking and recording signals is insufficient to determine a distance moved with a certain precision or confidence.

Figure 22:
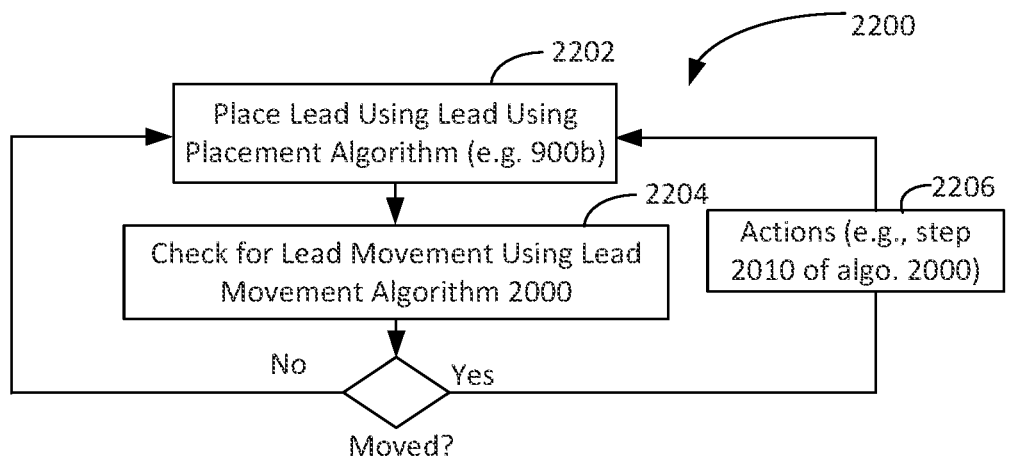
FIG. 22 illustrates a workflow using a lead movement detection algorithm during lead placement.

FIG. 22 illustrates an embodiment of using a lead movement algorithm 2000 to check for inadvertent lead movement during a process 2200 of placing a lead in a patient's brain. For example, a clinician may use a lead placement algorithm, such as the algorithm 900*b* (FIG. 9B) running on a system such as 1000 (FIG. 10) to assist in the lead placement procedure. The lead movement algorithm 2000 may also be running on the system 1000. At step 2202 the clinician is implanting a lead, assisted by a lead placement algorithm. As described above, the lead placement algorithm (e.g., 900*b*) may use features extracted from recorded EPs to help the clinician find a desirable or the optimum lead location. For example, the lead may be advanced until values for features extracted from the EPs match expected values for stimulation at the target location (see step 907 of algorithm 900*b*, FIG. 9B). During the execution of the lead placement algorithm, the lead movement algorithm 2000 may concurrently log and track the recorded EPs and/or EP features as they are recorded as the clinician advances the lead. At various times during the lead placement process the lead movement algorithm 2000 may check for inadvertent lead movement (step 2204). For example, the movement detection algorithm 2000 may check for inadvertent lead movement if the lead placement procedure is paused. If no lead movement is detected, then the lead placement procedure may be continued. If lead movement is detected, then the lead movement detection algorithm may take any of the actions described above (step 2206). For example, the lead movement detection algorithm may issue a warning to the user, etc.

Another example of when inadvertent lead movement may occur is during or following the process of anchoring the lead to patient's skull. For example, referring to algorithm 900*b* (FIG. 9B), assume that the clinician has completed step 907 and found the putative best lead placement based on the observed features of the EPs. As described above, steps 908 and 910 involve sweeping longitudinal and rotational locations upon the lead to find an optimal stimulation location, and then saving the parameters for use as input in further algorithms, such as sweet spot algorithms (e.g., algorithm 900*a*, FIG. 9A). Following those steps, the clinician may anchor the lead to the patient's skull, as is known in the art. According to some embodiments, the lead movement detection algorithm 2000 may check for lead movement before and/or after the anchoring process and take actions, as described above, if the lead has moved. When the lead being anchored is not the first lead to be anchored, the lead movement detection algorithm 2000 may check for lead movement of previously anchored leads.

Figure 23:
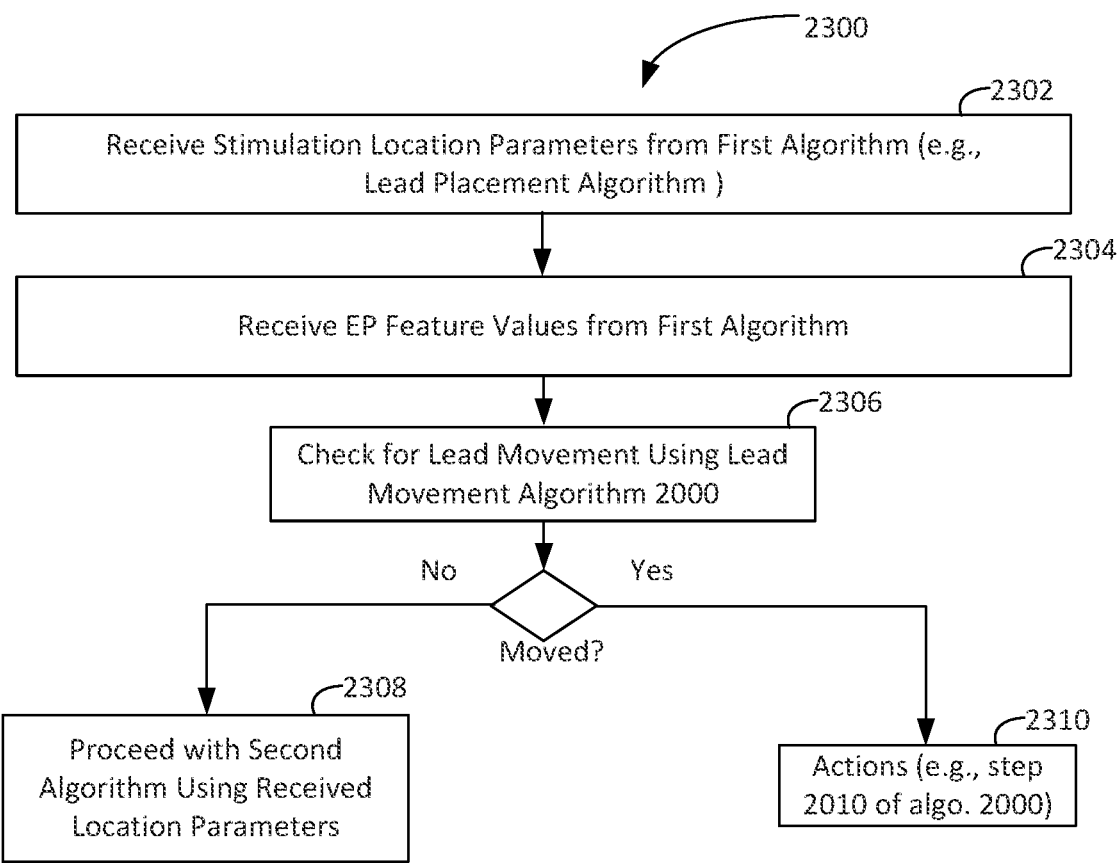
FIG. 23 illustrates a workflow using a lead movement detection algorithm during sweet spot searching.

FIG. 23 illustrates an embodiment of a workflow 2300 wherein the lead movement detection algorithm 2000 may be used to determine whether to use stimulation location parameters determined using a first algorithm as input into a second algorithm. For example, the first algorithm may be a lead placement algorithm, such as algorithm 900*b* (FIG. 9B). As explained above, once the lead is placed during the operating room procedure, an optimum stimulation location on the lead may be determined, for example by sweeping the longitudinal and rotational locations on the lead and determining values for EP features for each of the stimulation positions. The location parameters and corresponding EP feature values may be saved for later use as starting input in further procedures, such as sweet spot searching algorithms (e.g., algorithm 900*a*, FIG. 9A). At the time the second procedure (e.g., sweet spot searching procedure) is implemented, the location parameters determined during lead implantation can be used as input to provide a starting point or as a constraint for the second procedure. However, if the lead has inadvertently moved between the time the previous stimulation location parameters were determined and the time that the second procedure is executed, then those starting parameters may not be reliable.

In the illustrated workflow 2300, stimulation location parameters determined using a first algorithm are received at step 2302. At step 2304, values for recorded EPs evoked using the stimulation location parameters during the first algorithm are also received. At step 2306 the lead movement algorithm 2000 is used to determine if the lead has moved since the first location parameters and EP feature values were collected. For example, the lead movement algorithm may apply stimulation using the first location parameters and compare the resulting values for recorded EP features to those received from the first algorithm. If the lead movement algorithm determines that the lead has not moved, then the workflow proceeds to the second algorithm using the received location parameters as input (step 2308). If the lead movement algorithm determines that the lead has moved, then the lead movement algorithm may initiate actions as described above (step 2310).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of optimizing a position on an electrode lead implanted in a patient's brain for providing deep brain stimulation (DBS) to the patient's brain, the lead comprising a plurality of electrodes, the method comprising:
   (a) determining an optimized stimulation waveform for evoking a detectable evoked potential by:
      using one or more of the electrodes to provide an initial stimulation waveform, and
      adjusting one or more parameters of the initial stimulation waveform until first evoked potentials are detectable using one or more of the electrodes,
   (b) determining an optimized longitudinal stimulation position along an axis of the lead by:
      providing stimulation at different longitudinal positions along the axis of the lead using the optimized stimulation waveform,
      recording second evoked potentials evoked by the stimulation at each of the longitudinal positions,
      comparing each of the second evoked potentials with each other, and
      selecting the optimized longitudinal stimulation position based on the second evoked potentials, and
   (c) determining an optimized rotational stimulation position about the axis of the lead by:
      at the selected optimized longitudinal stimulation position providing stimulation at different rotational positions about the axis of the lead using the optimized stimulation waveform,
      recording third evoked potentials evoked by the stimulation at each of the rotational positions, and
      selecting the optimized rotational stimulation position based on the third evoked potential.

2. The method of claim 1, wherein the initial stimulation waveform comprises a first phase of a first polarity, as second phase of a second polarity, and an interphase interval.

3. The method of claim 1, wherein adjusting a parameter of the initial stimulation waveform comprises adjusting an amplitude of the waveform.

4. The method of claim 1, wherein providing stimulation at different longitudinal positions comprises fractionating current among two or more of the electrodes to provide stimulation at one or more virtual electrodes that are not co-located with any of the plurality of electrodes.

5. The method of claim 1, wherein providing stimulation at different rotational positions comprises fractionating current among two or more directional electrodes to provide stimulation at one or more virtual electrodes that are not co-located with any of the directional electrodes.

6. The method of claim 1, wherein selecting the optimized longitudinal position based on the second evoked potential comprises determining values for one or more features of the second evoked potentials and selecting the optimized longitudinal position based on the values.

7. The method of claim 1, wherein selecting the optimized rotational position based on the third evoked potential comprises determining values for one or more features of the third evoked potentials and selecting the optimized longitudinal position based on the values.

8. The method of claim 1, further comprising determining an indication that efficacy of therapy for the patient has declined and automatically performing the method in response to the indication.

9. The method of claim 8, wherein the indication that efficacy of therapy has declined is based, at least in part, on recorded evoked potentials that are recorded while the patient is undergoing DBS stimulation.

10. The method of claim 9, wherein the indication that efficacy of therapy has declined is based, at least in part, on impedances determined at one or more of the electrodes while the patient is undergoing DBS stimulation.

11. A medical device configured to optimize a position on an electrode lead implanted in a patient's brain for providing deep brain stimulation (DBS) to the patient's brain, the lead comprising a plurality of electrodes, the device comprising:
control circuitry configured to:
(a) determine an optimized stimulation waveform for evoking a detectable evoked potential by:
using one or more of the electrodes to provide an initial stimulation waveform, and
adjusting one or more parameters of the initial stimulation waveform until first evoked potentials are detectable using one or more of the electrodes,
(b) determine an optimized longitudinal stimulation position along an axis of the lead by:
providing stimulation at different longitudinal positions along the axis of the lead using the optimized stimulation waveform,
recording second evoked potentials evoked by the stimulation at each of the longitudinal positions,
comparing the each of the second evoked potentials with each other, and
selecting the optimized longitudinal stimulation position based on the second evoked potentials, and
(c) determine an optimized rotational stimulation position about the axis of the lead by:
at the selected optimized longitudinal stimulation position providing stimulation at different rotational positions about the axis of the lead using the optimized stimulation waveform,
recording third evoked potentials evoked by the stimulation at each of the rotational positions, and
selecting the optimized rotational stimulation position based on the third evoked potentials.

12. The device of claim 11, wherein the initial stimulation waveform comprises a first phase of a first polarity, as second phase of a second polarity, and an interphase interval.

13. The device of claim 11, wherein adjusting a parameter of the initial stimulation waveform comprises adjusting an amplitude of the waveform.

14. The device of claim 11, wherein providing stimulation at different longitudinal positions comprises fractionating current among two or more of the electrodes to provide stimulation at one or more virtual electrodes that are not co-located with any of the plurality of electrodes.

15. The device of claim 11, wherein providing stimulation at different rotational positions comprises fractionating current among two or more directional electrodes to provide stimulation at one or more virtual electrodes that are not co-located with any of the directional electrodes.

16. The device of claim 11, wherein selecting the optimized longitudinal position based on the second evoked potential comprises determining values for one or more features of the second evoked potentials and selecting the optimized longitudinal position based on the values.

17. The device of claim 11, wherein selecting the optimized rotational position based on the third evoked potential comprises determining values for one or more features of the third evoked potentials and selecting the optimized longitudinal position based on the values.

18. The device of claim 11, configured to determine an indication that efficacy of therapy for the patient has declined and automatically performing the method in response to the indication.

19. The device of claim 18, wherein the indication that efficacy of therapy has declined is based, at least in part, on recorded evoked potentials that are recorded while the patient is undergoing DBS stimulation.

20. The device of claim 19, wherein the indication that efficacy of therapy has declined is based, at least in part, on impedances determined at one or more of the electrodes while the patient is undergoing DBS stimulation.

\* \* \* \* \*